United States Patent
Morris

(10) Patent No.: US 11,026,913 B2
(45) Date of Patent: Jun. 8, 2021

(54) NUTRITIONAL FORMULAS COMPRISING MEDIUM CHAIN FATTY ACIDS OR ESTERS THEREOF AND METHODS RELATED THERETO

(71) Applicants: Emory University, Atlanta, GA (US); Children's Healthcare of Atlanta, Inc., Atlanta, GA (US)

(72) Inventor: Claudia R. Morris, Atlanta, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 436 days.

(21) Appl. No.: 14/916,634

(22) PCT Filed: Sep. 4, 2014

(86) PCT No.: PCT/US2014/053990
§ 371 (c)(1),
(2) Date: Mar. 4, 2016

(87) PCT Pub. No.: WO2015/034984
PCT Pub. Date: Mar. 12, 2015

(65) Prior Publication Data
US 2016/0199337 A1 Jul. 14, 2016

Related U.S. Application Data

(60) Provisional application No. 61/873,865, filed on Sep. 5, 2013.

(51) Int. Cl.
| | |
|---|---|
| *A61K 31/23* | (2006.01) |
| *A61K 31/202* | (2006.01) |
| *A61K 31/122* | (2006.01) |
| *A61K 31/07* | (2006.01) |
| *A61K 31/59* | (2006.01) |
| *A61K 38/46* | (2006.01) |
| *A61K 31/7004* | (2006.01) |

(Continued)

(52) U.S. Cl.
CPC .............. *A61K 31/23* (2013.01); *A23L 33/12* (2016.08); *A23L 33/135* (2016.08); *A23L 33/15* (2016.08); *A23L 33/155* (2016.08); *A23L 33/16* (2016.08); *A23L 33/175* (2016.08); *A23L 33/40* (2016.08); *A61K 9/0056* (2013.01); *A61K 31/047* (2013.01); *A61K 31/07* (2013.01); *A61K 31/122* (2013.01); *A61K 31/19* (2013.01); *A61K 31/20* (2013.01); *A61K 31/202* (2013.01); *A61K 31/205* (2013.01); *A61K 31/22* (2013.01); *A61K 31/231* (2013.01); *A61K 31/232* (2013.01); *A61K 31/355* (2013.01); *A61K 31/375* (2013.01); *A61K 31/385* (2013.01); *A61K 31/4375* (2013.01); *A61K 31/473* (2013.01); *A61K 31/59* (2013.01); *A61K 31/661* (2013.01); *A61K 31/7004* (2013.01); *A61K 33/18* (2013.01); *A61K 33/24* (2013.01); *A61K 33/26* (2013.01); *A61K 33/30* (2013.01); *A61K 33/32* (2013.01); *A61K 33/34* (2013.01); *A61K 33/42* (2013.01); *A61K 35/741* (2013.01); *A61K 38/46* (2013.01); *A61K 45/06* (2013.01); *A23V 2002/00* (2013.01); *A61K 9/145* (2013.01); *A61K 9/2013* (2013.01); *A61K 9/4858* (2013.01); *A61K 2035/115* (2013.01)

(58) Field of Classification Search
CPC ...... A61K 31/23; A61K 31/355; A61K 31/22; A61K 33/42; A61K 45/06; A61K 31/19; A61K 31/4375; A61K 31/231; A61K 9/0056; A61K 31/232; A61K 31/20; A61K 31/202; A61K 31/122; A61K 31/07; A61K 31/59; A61K 38/46; A61K 31/7004; A61K 31/473; A61K 35/741; A61K 33/26; A61K 31/661; A61K 33/18; A61K 33/34; A61K 33/32; A61K 33/24; A61K 31/047; A61K 31/385; A61K 31/205; A61K 31/375; A61K 33/30; A61K 9/2013; A61K 9/145; A61K 9/4858; A61K 2035/115; A23L 33/175; A23L 33/15; A23L 33/12; A23L 33/40; A23L 33/16; A23L 33/155; A23L 33/135; A23V 2002/00
See application file for complete search history.

(56) References Cited

U.S. PATENT DOCUMENTS

| | | | | |
|---|---|---|---|---|
| 4,778,794 | A | * | 10/1988 | Naruse .................... A61P 43/00 514/249 |
| 4,959,350 | A | | 9/1990 | Frokjaer |

(Continued)

OTHER PUBLICATIONS

Krigsman, ("Gastrointestianl Pathology in Autism: Description and Treatment", Medical Veritas, 4 (2007), 1528-1536). (Year: 2007).*

(Continued)

*Primary Examiner* — Louise W Humphrey
*Assistant Examiner* — Anjali Ajit Hirani
(74) *Attorney, Agent, or Firm* — Emory Patent Group

(57) ABSTRACT

This disclosure relates to nutritional formulas and uses for treating or preventing a gastrointestinal condition and/or motor-planning speech and/or coordinator difficulties. In certain embodiments, this disclosure relates to a nutritional formula comprising medium 5 chain fatty acids, or esters thereof (such as and tri-, di-, mono-glycerides, or alkyl esters), unsaturated fatty acids, and a vitamin E and optionally other nutrients. In certain embodiments, any of the compounds or nutrients may be in alternative salt forms.

19 Claims, 1 Drawing Sheet

(51) Int. Cl.

| | | |
|---|---|---|
| A61K 31/473 | (2006.01) | |
| A61K 35/741 | (2015.01) | |
| A61K 33/26 | (2006.01) | |
| A61K 31/661 | (2006.01) | |
| A61K 33/18 | (2006.01) | |
| A61K 33/34 | (2006.01) | |
| A61K 33/32 | (2006.01) | |
| A61K 33/24 | (2019.01) | |
| A61K 31/047 | (2006.01) | |
| A61K 31/385 | (2006.01) | |
| A61K 31/205 | (2006.01) | |
| A61K 31/375 | (2006.01) | |
| A61K 33/30 | (2006.01) | |
| A61K 31/355 | (2006.01) | |
| A23L 33/175 | (2016.01) | |
| A23L 33/15 | (2016.01) | |
| A23L 33/12 | (2016.01) | |
| A61K 31/22 | (2006.01) | |
| A61K 33/42 | (2006.01) | |
| A23L 33/00 | (2016.01) | |
| A61K 45/06 | (2006.01) | |
| A23L 33/16 | (2016.01) | |
| A61K 31/19 | (2006.01) | |
| A61K 31/4375 | (2006.01) | |
| A23L 33/155 | (2016.01) | |
| A61K 31/231 | (2006.01) | |
| A61K 9/00 | (2006.01) | |
| A61K 31/232 | (2006.01) | |
| A61K 31/20 | (2006.01) | |
| A23L 33/135 | (2016.01) | |
| A61K 35/00 | (2006.01) | |
| A61K 9/20 | (2006.01) | |
| A61K 9/14 | (2006.01) | |
| A61K 9/48 | (2006.01) | |

(56) References Cited

U.S. PATENT DOCUMENTS

| | | | | |
|---|---|---|---|---|
| 5,444,054 | A * | 8/1995 | Garleb | A23L 33/40 426/72 |
| 5,922,766 | A | 7/1999 | Acosta | |
| 5,977,175 | A | 11/1999 | Lin | |
| 6,258,387 | B1 | 7/2001 | McEwen | |
| 6,426,362 | B1 | 7/2002 | Miller | |
| 9,687,016 | B2 | 6/2017 | Morris | |
| 2005/0249823 | A1 | 11/2005 | Murphy | |
| 2008/0213239 | A1* | 9/2008 | Morris | A23L 33/12 424/94.1 |
| 2009/0075862 | A1 | 3/2009 | Boza | |
| 2011/0009357 | A1* | 1/2011 | Hageman | A61K 31/19 514/51 |
| 2011/0027348 | A1 | 2/2011 | Feher | |

OTHER PUBLICATIONS

Wasilewska, ("Gastrointestinal abnormalities in children with autism (English Title)", Polski Merkuriusz Lekarski: Organ Polskiego Towarzystwa Lekarskiego, Jul. 27, 2009(157), 40-43) (Year: 2009).*

Buie ("Evaluation, Diagnosis, and Treatment of Gastrointestinal Disorders in Individual With ASDs: A Consensus Report", Pediatrics, vol. 125, Supplement 1, Jan. 2010) (Year: 2010).*

Aoyagi et al., Enteral Nutrition as a Primary Therapy for Intestinal Lymphangiectasia: Value of Elemental Diet and Polymeric Diet Compared with Total Parenteral Nutrition, Digestive Diseases and Sciences, vol. 50, No. 8 (Aug. 2005), pp. 1467-1470.

Buie et al. Evaluation, Diagnosis, and Treatment of Gastrointestinal Disorders in Individuals With ASDs: A Consensus Report, Pediatrics. 2010,125 Suppl 1:S1-18.

Buie et al. Recommendations for Evaluation and Treatment of Common Gastrointestinal Problems in Children With ASDs, Pediatrics. Jan. 2010;125 Suppl 1:S19-29.

McClave et al. Guidelines for the Provision and Assessment of Nutrition Support Therapy in the Adult Critically Ill Patient, JPEN J Parenter Enteral Nutr. 2009, 33(3):277-316.

Morris et al. Syndrome of Allergy, Apraxia, and Malabsorption: Characterization of a Neurodevelopmental Phenotype That Responds to Omega 3 and Vitamin E Supplementation, Altern Ther Health Med. 2009;15(4):34-437.

Shah et al. Lipid-Based Isotropic Solutions: Design Considerations, Chapter 6, pp. 129-134, in Hauss, Oral Lipid-Based Formulations: Enhancing the Bioavailability of Poorly Water-Soluble Drugs, 2007.

"Speak TM—Speech Nutrients", available online at http://www.speechnutrients.com/products/speak on Nov. 4, 2013.

Williams et al. Impaired Carbohydrate Digestion and Transport and Mucosal Dysbiosis in the Intestines of Children with Autism and Gastrointestinal Disturbances, 2011, PLoS ONE 6(9): e24585.

Freeman et al. Intestinal lymphangiectasia in adults, World J Gastrointest Oncol 2011, 3(2): 19-23.

Jeffries et al. Low-Fat Diet in Intestinal Lymphangiectasia. Its Effect on Albumin Metabolism. N Engl J Med. 1964, 270:761-6.

Croonenberghs et al. Serotonergic disturbances in autistic disorder: L-5-hydroxytryptophan administration to autistic youngsters increases the blood concentrations of serotonin in patients but not in controls, Life Sciences 76 (2005) 2171-2183.

Frye et al. Tetrahydrobiopterin as a Novel Therapeutic Intervention for Autism, Neurotherapeutics. 2010, 7(3): 241-249.

Herbert et al. Autism and Dietary Therapy: Case Report and Review of the Literature, Journal of Child Neurology, 2013 28(8) 975-982.

Hollis et al. Medium chain triglyceride diet reduces anxiety-like behaviors and enhances social competitiveness in rats, Neuropharmacology 138 (2018) 245e256.

* cited by examiner

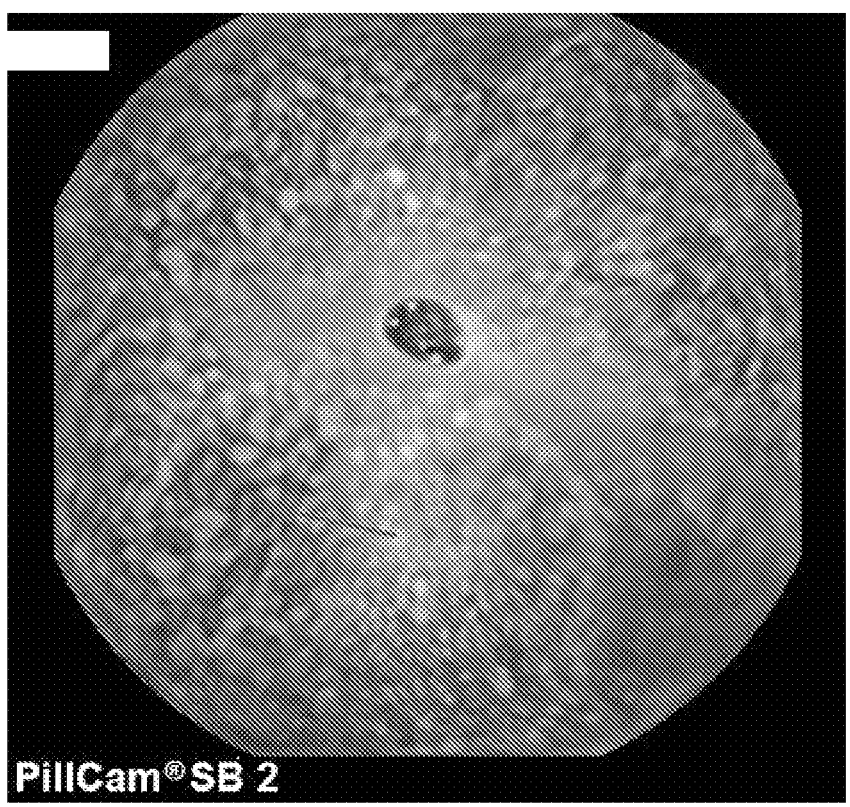

NUTRITIONAL FORMULAS COMPRISING MEDIUM CHAIN FATTY ACIDS OR ESTERS THEREOF AND METHODS RELATED THERETO

CROSS-REFERENCE TO RELATED APPLICATIONS

This Application is the National Stage of International Application Number PCT/US2014/053990 filed Sep. 4, 2014, which claims priority to U.S. Provisional Application No. 61/873,865 filed Sep. 5, 2013. The entirety of each of these applications is hereby incorporated by reference for all purposes.

BACKGROUND

Autism spectrum disorders (ASD) are typically defined by impairments in verbal and non-verbal communication, social interactions, and repetitive behaviors. Gastrointestinal (GI) symptoms are common in individuals with ASD. See Williams et al., PLoS ONE, 2011, 6(9): e24585. The total or partial inability to plan verbal movement, common in autism spectrum disorders, is diagnosed as verbal apraxia or dyspraxia. Morris & Agin report that children with verbal apraxia responded to polyunsaturated fatty acids and Vitamin E supplementation. Altern Ther Health Med, 2009, 15(4):34-43. See also US Published Patent Application Number 2008/0213239 and US 2009/0075862.

Intestinal lymphangiectasia is a rare disease that is characterized by lymphatic vessel dilation, diarrhea, and loss of protein and immune dysregulation. It is considered to be a chronic form of protein-losing enteropathy. Aoyagi et al. report that enteral nutrition appears to be as effective as total parenteral nutrition for human patients with intestinal lymphangiectasia. Digestive Diseases and Sciences, 2005, 50(8): 1467-1470.

McClave et al. report guidelines for the provision and assessment of nutrition support therapy for adult critically ill patients. J Parenter Enteral Nutr, 2009, 33(3):277-316.

See also. U.S. Pat. Nos. 6,258,387, 5,922,766, and 4,959, 350.

References cited herein are not an admission of prior art.

SUMMARY

This disclosure relates to nutritional formulas and uses for treating or preventing a gastrointestinal condition and/or motor-planning speech and/or coordinator difficulties. In certain embodiments, this disclosure relates to a nutritional formula comprising medium chain fatty acids, or esters thereof (such as and tri-, di-, mono-glycerides, or alkyl esters), unsaturated fatty acids, and a vitamin E and optionally other nutrients. In certain embodiments, any of the compounds or nutrients may be in alternative salt forms.

In certain embodiments, the disclosure relates to a dietary formulation comprising: a) medium chain fatty acid, glycerol ester, or alkyl ester thereof, b) an omega-3 fatty acid, alkyl ester thereof, or glycerol ester thereof, and c) a vitamin E isomer.

In certain embodiments, the glycerol ester of the medium chain fatty acid is selected from glycerol tricaprate, glycerol, dicaprate, glycerol monocaprate, glycerol tricaprylate, glycerol dicaprylate, glycerol monocaprylate, and glycerol trihexanoate, or combinations thereof.

In certain embodiments, the medium chain fatty acid or alkyl ester thereof is selected from capric acid, ethyl caprate, caprylic acid, ethyl caprylate, hexanoic acid, and ethyl hexanoate, or combinations thereof.

In certain embodiments, the nutritional formula further comprises a lauric acid or ester thereof selected from glycerol trilaurate, glycerol dilaurate, glycerol monolaurate, lauric acid, ethyl laurate, or saturated or unsaturated fatty acid chains of greater than 12 carbons or combinations thereof.

In certain embodiments, the nutritional formula comprises coconut oil, palm kernel oil or combinations thereof.

In certain embodiments, the omega-3 fatty acid or alkyl ester thereof is selected from alpha-linolenic acid, eicosapentaenoic acid, docosahexaenoic acid, ethyl linolenate, ethyl eicosapentaenoate, and ethyl docosahexaenoate or combinations thereof. In certain embodiments, the formula comprises eicosapentaenoic acid and docosahexaenoic acid, wherein the ratio of eicosapentaenoic acid and docosahexaenoic acid is in a range of from about 1.5:1 to about 5:1.

In certain embodiments, the vitamin E isomer is selected from alpha-tocopherol and gamma-tocopherol or a combination thereof, wherein the alpha-tocopherol is present in an amount of from about 500 mg to about 3000 mg per unit dose, and the gamma-tocopherol is present in an amount of from about 200 mg to about 1000 mg per unit dose.

In certain embodiments, the disclosure relates to a dietary formulation comprising: a) medium chain fatty acid, glycerol ester, or alkyl ester thereof, b) an omega-3 fatty acid, alkyl ester thereof, or glycerol ester thereof, c) a vitamin E isomer and d) a vitamin K.

In certain embodiments, the disclosure relates to a dietary formulation comprising medium chain fatty acid, glycerol ester, or alkyl ester thereof, eicosapentaenoic acid, docosahexaenoic acid, alpha tocopherol, gamma tocopherol, phytonadione, and gamma-linolenic acid.

In certain embodiments, the disclosure relates to a dietary formulation comprising: a) medium chain fatty acid, glycerol ester, or alkyl ester thereof, b) an omega-3 fatty acid, alkyl ester thereof, or glycerol ester thereof, c) a vitamin A isomer, d) a vitamin D, e) vitamin E isomer and f) a vitamin K.

In certain embodiments, the disclosure relates to a dietary formulation comprising medium chain fatty acid, glycerol ester, or alkyl ester thereof, eicosapentaenoic acid, docosahexaenoic acid, retinoic acid, cholecalciferol, ergocalciferol, alpha tocopherol, gamma tocopherol, phytonadione, and gamma-linolenic acid.

In certain embodiments, the formula comprises further comprises a component selected from long chain fatty acids, esters of long chain fatty acids, alpha-lipoid acid, a carnitine, probiotics, an omega-6 fatty acid, an esters of omega-6 fatty acid, gamma-linolenic acid, ethyl gamma-linolenate, an omega-9 fatty acid, esters of omega-9 fatty acid, oleic acid, ethyl oleate, zinc, calcium, magnesium, selenium, a vitamin A, a vitamin $B_1$, a vitamin $B_2$, a vitamin $B_3$, a vitamin $B_5$, a vitamin $B_6$, a vitamin $B_7$, a vitamin $B_9$, a vitamin $B_{12}$, vitamin C, vitamin D, vitamin K, S-adenosylmethionine, a phosphocholine, creatine, a coenzyme Q, taurine, tetrahydrobiopterin, methylcobalamin, betaine, pancreatic enzymes, folinic acid, pancrelipase, a leukotriene inhibitor, a arginine, glutamine, N-acetylcysteine, an anti-fungal agent, berberine, an anti-inflammatory agent, anti-bacterial agent, anti-oxidant, saccharides and polysaccharides or combinations thereof.

In certain embodiments, the formulation is in a dosage form selected from a tablet, a capsule, a powder, a gel, and a liquid. In certain embodiments, dietary formulas disclosed herein comprise one or more food-grade components.

In certain embodiments, the disclosure relates to a dietary formulation comprising: a) medium chain fatty acid, glycerol ester, or alkyl ester thereof, b) an omega-3 fatty acid, alkyl ester thereof, or glycerol ester thereof, and c) a vitamin E isomer. In certain embodiments the omega-3 ester is the ethyl ester of eicosapentaenoic acid. In certain embodiments, the medium chain fatty glycol ester is a mixture of glycol esters of caprylic acid and capric acid. In certain embodiments, the ratio of glycerol esters of caprylic acid and capric acid is 1:1 to 4:1, or 1:1 to 5:1, or 1:1.5 to 1:3 by weight respectively.

In certain embodiments, the formula further comprises berberine and pancreatic enzymes.

In certain embodiments, the formula further comprises L-amino acids and not peptides or proteins.

In certain embodiments, the disclosure relates to a dietary formulation comprising formulations reported herein in combination with a source of glucose, malodextrin, cornstarch, or combinations thereof. In certain embodiments, the formula further comprises monosaccharides such as glucose, fructose, and galactose and optionally disaccharides, but typically not larger polysaccharides. In certain embodiments, this formulation is contemplated for subjects with fructose malabsorption or a primary lactase deficiency that is genetic due to environmental causes.

In certain embodiments, the disclosure relates to a dietary formulation comprising formulations reported herein in combination with 5-hydroxytryptophan present in an amount of from about 10 mg to about 100 mg per unit dose, sulforaphane present in an amount of from about 500 µg to about 5000 µg per unit dose, curcumin present in an amount of from about 50 mg to about 2500 mg per unit dose, or combinations thereof.

In certain embodiments, the disclosure relates to a dietary formulation comprising formulations reported herein in combination with L-amino acids and not peptides or proteins. In certain embodiments, the formulation does not contain phenylalanine.

In certain embodiments, the disclosure relates to a dietary formulation comprising formulations reported herein in combination with a probiotic or berberine.

In certain embodiments, the disclosure relates to a dietary formulation comprising formulations reported herein in combination with iron present in an amount of from about 2.5-10 mg per unit dose, phosphorus present in an amount of from about 200-850 mg per unit dose, iodine present in an amount of from about 30-120 µg per unit dose, copper present in an amount of from about 0.25-1.0 mg per unit dose, manganese present in an amount of from about 0.5-2.0 mg per unit dose, chromium present in an amount of from about 10-45 µg per unit dose, molybdenum present in an amount of from about 15-100 µg per unit dose, inositol present in an amount of from about 10-1000 mg per unit dose, or combinations thereof.

In certain embodiments, the disclosure relates to methods of treating or preventing apraxia and/or autism spectrum disorder, the method comprising orally administering to an individual in need thereof an effective amount of a dietary formula disclosed herein. In certain embodiments, the disclosure relates to methods the subject is diagnosed with intestinal lymphangiectasia.

In certain embodiments, the disclosure relates to methods of treating or preventing small bowel inflammation and conditions lending to small bowel bacterial overgrowth that induce fat malabsorption, the method comprising orally administering to an individual in need thereof an effective amount of a dietary formula disclosed herein to a subject in need thereof.

BRIEF DESCRIPTION OF THE FIGURES

FIG. 1 shows video pill cam indicating erythema and white nodules in the jejunum. The white villi and/or spots (dilated lacteals), white nodules in the jejunum are observed on video capsule endoscopy are consistent with the diagnosis of intestinal lymphangiectasia. This taken together with a long-standing history of fat malabsorption, neurological symptoms of vitamin E deficiency, a protein-losing enteropathy with previously unexplained hypoalbuminemia, multiple micronutrient and vitamin deficiencies (zinc, iron, vitamin D, B12 etc), short stature, edema of the ankles and hands, hypocholesterolemia (cholesterol<100), and vulnerability to infections suggesting immune dysregulation (chronic thrush, disseminated molluscum contagiosum, recurrent skin, ear and sinus infections) explains the dramatic response to nutritional interventions in this child.

DETAILED DISCUSSION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "an omega-3 fatty acid" includes a plurality of such fatty acids and reference to "the vitamin E" includes reference to one or more vitamin E isoforms and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, "subject" refers to any animal, typically a human patient, livestock, or domestic pet such as a dog.

As used herein, the terms "prevent" and "preventing" include the prevention of the recurrence, spread or onset. It is not intended that the present disclosure be limited to complete prevention. In some embodiments, the onset is delayed, or the severity of the disease or condition is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

"Fatty acids" refers to a family of carboxylic acids having a saturated or unsaturated hydrocarbon chain of about 4 to about 28 carbons in length, and is intended to include carboxylic acid salt forms.

Medium chain fatty acids (MCFAs) refer to a family of carboxylic acids having a saturated or unsaturated hydrocarbon chain of from about 6 to 10 carbons in length, and is intended to include carboxylic acid salt forms. Examples include capric acid, caprylic acid, and hexanoic acid. Medium-chain triglycerides (MCTs) are esters (tri-, di-, monoglyceride esters) of medium chain fatty acids and glycerol. Natural sources of MCFAs and MCTs include coconut, palm kernel oil, and bovine milk. One method of producing MCT is by hydrolysis of coconut or palm kernel oil, filtration of MCFAs, and subsequent re-esterification of the MCFAs with glycerol. Oils produced by re-esterification contain mostly caprylic acid (octanoic) and capric acid (decanoic acid), at a ratio from about 50:50 to 80:20 with typically less than 5% of long chain or shorter chain acids.

Long chain fatty acids are typically between 12 and 28 carbons in length. Unsaturated fatty acids have at least one carbon-carbon double bond in the hydrocarbon chain. Unsaturated fatty acids include monounsaturated fatty acids and polyunsaturated fatty acids (PUFAs). Unsaturated fatty acids are designated by the position of the first double bond from the methyl end of the hydrocarbon chain.

Omega-3 fatty acids have a first double bond at the third carbon from the methyl end of the chain; and include, e.g., alpha-linolenic acid (octadeca-9,12,15-trienoic acid), stearidonic acid (octadeca-6,9,12,15-tetraenoic acid), eicosapentaenoic acid (eicosa-5,8,11,14,17-pentaenoic acid; "EPA"), docosapentaenoic acid (docosa-7,10,13,16,19-pentaenoic acid), eicosatetraenoic acid (eicosa-8,11,14,17-tetraenoic acid), and docosahexaenoic acid (docosa-4,7,10,13,16,19-hexaenoic acid; "DHA"). Ethyl eicosapentaenoate, icosapent ethyl (Vascepa™) is an omega-3 polyunsaturated fatty acid (PUFA) ester composition FDA approved for the treatment of hypertriglyceridemia.

Omega-6 fatty acids have a first double bond at the sixth carbon from the methyl end of the chain; and include, e.g., linoleic acid (9,12-octadecadienoic acid), gamma-linolenic acid (6,9,12-octadecatrienoic acid; GLA), eicosadienoic acid (11,14-eicosadienoic acid), dihomo-gamma-linolenic acid (8,11,14-eicosatrienoic acid), arachidonic acid (5,8,11,14-eicosatetraenoic acid), docosadienoic acid (13,16-docosadienoic acid), adrenic acid (7,10,13,16-docosatetraenoic acid), docosapentaenoic acid (4,7,10,13,16-docosapentaenoic acid), and calendic acid (8E,10E,12Z-octadecatrienoic acid), and the like. Omega-9 fatty acids have a first double bond at the ninth carbon from the methyl end of the chain; and include, e.g., oleic acid (cis-9-octadecenoic acid); eicosenoic acid (cis-11-eicosenoic acid); mead acid (all-cis-5,8,11-eicosatrienoic acid); erucic acid (cis-13-docosenoic acid); and nervonic acid (cis-15-tetracosenoic acid).

As used herein, a "vitamin E" refers to a family of eight molecules having a chromanol ring (chroman ring with an alcoholic hydroxyl group) and a 12-carbon aliphatic side chain containing two methyl groups in the middle and two more methyl groups at the end. The side chain of the tocopherols is saturated, while the side chain of the tocotrienols contain three double-bonds, all of which adjoin a methyl group. The tocopherols and the tocotrienols exist in four isoforms, referred to as alpha, beta, gamma and delta isoforms. The isoforms are named on the basis of the number and position of the methyl groups on the chromanol ring. The alpha form has three methyl groups, the beta and gamma forms have two methyl groups and the delta for has only one methyl group. A "vitamin E" may be alpha-tocopherol, beta-tocopherol, gamma-tocopherol, alpha-tocotrienol, beta-tocotrienol, and gamma-tocotrienol. A "vitamin E" also includes esters of a vitamin E isoform. For example, a "vitamin E" includes esters of a tocopherol, including acetates and succinates.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butyryl, 2-butyryl, 1-pentynyl, 2-pentynyl, 3-methyl-1-butyryl, and the like.

As used herein, the term a "lipoic acid" refers to alpha-lipoic acid, which is a chiral molecule also known as 6,8-dithioloctanoic acid. Unless specified the term "lipoic acid" encompasses the racemic mixture as well as any other (non-50/50) mixture of the enantiomers including substantially pure forms of either the R-(+) or the S-(−) enantiomer. Further, unless specified otherwise the term covers salts (e.g. Na and K salts) and amides, esters and metabolites of the acid.

"Carnitine" is also known as 3-hydroxy-4-(trimethylazaniumyl)butanoate. As used herein, the term a "carnitine" includes carnitine and "carnitine analogs" and encompasses racemic or essentially pure L-carnitine (carnitine), or a corresponding alkanoyl-carnitine such as acetyl-carnitine or propionyl-carnitine, or a suitable salt of such compounds such as L-carnitine tartrate, L-carnitine fumarate, L-carnitine-magnesium-citrate, acetyl-L-carnitine tartrate, acetyl-L-carnitine-magnesium-citrate, or any mixture of the aforementioned compounds.

Formulations

The present disclosure provides for dietary formulations comprising medium chain fatty acids, or esters thereof, such as and tri-, di-, monoglycerides, or alkyl esters, unsaturated fatty acids such as omega 3 fatty acids, and a vitamin E and optionally other nutrients.

Suitable medium chain fatty acids, or esters thereof, such as and tri-, di-, monoglycerides, or alkyl esters include glycerol tricaprate, glycerol, dicaprate, glycerol monocaprate, glycerol tricaprylate, glycerol dicaprylate, glycerol monocaprylate, and glycerol trihexanoate, capric acid, ethyl caprate, caprylic acid, ethyl caprylate, hexanoic acid, and ethyl hexanoate, or combinations thereof.

It is contemplated that these medium chain fatty acids may be obtained from coconut oil and palm kernel oil. For example, some processes of abstracting medium chain fatty acids from coconut oil result in compositions containing medium chain fatty acids and glycerol esters with about 3% caproic acid, and about 65% caprylic acid, and capric acid 30%, and about less than 1% lauric acid and other long chain fatty acids. In certain embodiments, the nutritional formula further comprises a lauric acid or ester thereof selected from glycerol trilaurate, glycerol dilaurate, glycerol monolaurate, lauric acid, ethyl laurate, or saturated or unsaturated fatty acid chains of greater than 12 carbons or combinations thereof. Typically the lauric acid and other long chain fatty acids are less than 2% or less than 1% by weight total weight of fatty acids.

Suitable unsaturated fatty acids include, but are not limited to, omega-3 fatty acids and omega-6 fatty acids. Suitable omega-3 fatty acids include, e.g., a-linolenic acid (octadeca-9,12,15-trienoic acid), stearidonic acid (octadeca-6,9,12,15-tetraenoic acid), eicosapentaenoic acid (eicosa-5,8,11,14,17-pentaenoic acid; "EPA"), docosapentaenoic acid (docosa-7,10,13,16,19-pentaenoic acid), eicosatetraenoic acid (eicosa-8,11,14,17-tetraenoic acid), and docosahexaenoic acid (docosa-4,7,10,13,16,19-hexaenoic acid; "DHA"). Suitable omega-6 fatty acids include, e.g., linoleic acid (9,12-octadecadienoic acid), gamma-linolenic acid (6,9,12-octadecatrienoic acid; GLA), eicosadienoic acid (11,14-eicosadienoic acid), dihomo-gamma-linolenic acid (8,11,14-eicosatrienoic acid), arachidonic acid (5,8,11,14-eicosatetraenoic acid), docosadienoic acid (13,16-docosadienoic acid), adrenic acid (7,10,13,16-docosatetraenoic acid), docosapentaenoic acid (4,7,10,13,16-docosapentaenoic acid), and calendic acid (8E,10E,12Z-octadecatrienoic acid).

A contemplated formulation can comprise one, two, three, four, five, six, seven, or eight different vitamin E isoforms. For example, in some embodiments, a subject formulation comprises alpha-tocopherol and gamma-tocopherol; and substantially no other vitamin E isoforms. In other embodiments, a subject formulation includes alpha-tocopherol, gamma-tocopherol, and at least one other vitamin E isoform. For example, in some embodiments, a subject formulation includes alpha-tocopherol, gamma-tocopherol, and at least one of beta-tocopherol, delta-tocopherol, alpha-tocotrienol, beta-tocotrienol, gamma-tocotrienol, and delta-tocotrienol. In other embodiments, a subject formulation includes alpha-tocopherol, gamma-tocopherol, beta-tocopherol, delta-tocopherol, alpha-tocotrienol, beta-tocotrienol, gamma-tocotrienol, and delta-tocotrienol.

In some embodiments, a contemplated formulation comprises at least one medium chain fatty acid or ester, at least one omega-3 fatty acid; and at least one vitamin E isoform. In some embodiments, a contemplated formulation comprises two different omega-3 fatty acids. In some embodiments, a contemplated formulation comprises eicosapentaenoic acid (EPA); docosahexaenoic acid (DHA); and at least one vitamin E isoform. In certain embodiments, the ratio of EPA to DHA can range from about 1.5:1 (EPA:DHA) to about 5:1 (EPA:DHA), where the ratio is on a weight basis. For example, the EPA:DHA ratio can range from about 1.5:1 to about 2:1, from about 2:1 to about 2.5:1, from about 2.5:1 to about 3:1, from about 3:1 to about 3.5:1, from about 3.5:1 to about 4:1, from about 4:1 to about 4.5:1, or from about 4.5:1 to about 5:1. In some embodiments, the EPA:DHA ratio is 2.5:1. When considering weight ratios of salts the, non-salt form is contemplated.

In some embodiments, a contemplated formulation comprises at least one medium chain fatty acid or ester or at least two medium chain fatty acid or ester; at least one omega-3 fatty acids; at least one vitamin E isoform; and at least one omega-6 fatty acid. For example, in some embodiments, a contemplated formulation comprises medium chain fatty acids or esters or coconut oil; EPA; DHA; and at least one omega-6 fatty acid. In some embodiments, a contemplated formulation comprises medium chain fatty acids or esters or coconut oil; EPA; DHA; at least one vitamin E isoform; and gamma-linolenic acid (GLA). In some embodiments, a contemplated formulation comprises medium chain fatty acids or esters or coconut oil; EPA; DHA; alpha-tocopherol; gamma-tocopherol; and GLA.

In some embodiments, a contemplated formulation comprises medium chain fatty acids or esters or coconut oil; at least two different omega-3 fatty acids; at least one vitamin E isoform; and an omega-9 fatty acid. In some embodiments, a contemplated formulation comprises medium chain fatty acids or esters or coconut oil; at least two different omega-3 fatty acids; at least one vitamin E isoform; an omega-6 fatty acid; and an omega-9 fatty acid. The omega-9 fatty acid is in some embodiments a monounsaturated fatty acid. In some embodiments, the omega-9 fatty acid is oleic acid.

Lipoic Acid

In some embodiments, a contemplated formulation comprises medium chain fatty acids or esters or coconut oil and a lipoic acid. Thus, e.g., in some embodiments, a contemplated formulation comprises medium chain fatty acids or esters or coconut oil; a long chain fatty acid or ester; at least one vitamin E isoform; and alpha-lipoic acid. In some embodiments, a contemplated formulation comprises medium chain fatty acids or esters or coconut oil; at least one omega-3 fatty acid; at least one vitamin E isoform; and alpha-lipoic acid. For example, in some embodiments, a contemplated formulation comprises medium chain fatty acids or esters or coconut oil; EPA; DHA; at least one vitamin E isoform; and alpha-lipoic acid. In some embodiments, a contemplated formulation comprises medium chain fatty acids or esters or coconut oil; EPA; DHA; alpha-tocopherol; gamma-tocopherol; and alpha-lipoic acid. In other embodiments, a contemplated formulation comprises medium chain fatty acids or esters or coconut oil; at least one omega-3 fatty acid; an omega-6 fatty acid; at least one vitamin E isoform; and alpha-lipoic acid. For example, in some embodiments, a contemplated formulation comprises medium chain fatty acids or esters or coconut oil; EPA; DHA; GLA; alpha-tocopherol; gamma-tocopherol; and alpha-lipoic acid.

The alpha-lipoic acid can exist as an about 50/50 or racemic mixture of R-(+)-alpha-lipoic acid and S-(−)-alpha-lipoic acid. The alpha-lipoic acid ingredient of a contemplated formulation can be about 100% R-(+) enantiomer. However, the alpha-lipoic acid can be present in a contemplated formulation in any mixture of the two enantiomers e.g. 10% S-(−) and 90% R-(+); 25% S-(−) and 75% R-(+); etc.

Carnitine

In some embodiments, a contemplated formulation comprises medium chain fatty acids or esters or coconut oil and carnitine. Thus, e.g., in some embodiments, a contemplated formulation comprises medium chain fatty acids or esters or coconut oil; long chain fatty acid; at least one vitamin E isoform; and carnitine. In some embodiments, a contemplated formulation comprises medium chain fatty acids or esters or coconut oil; at least one omega-3 fatty acid; at least one vitamin E isoform; and carnitine. For example, in some embodiments, a contemplated formulation comprises medium chain fatty acids or esters or coconut oil; EPA; DHA; at least one vitamin E isoform; and carnitine. In some embodiments, a contemplated formulation comprises medium chain fatty acids or esters or coconut oil; EPA; DHA; alpha-tocopherol; gamma-tocopherol; and carnitine. In other embodiments, a contemplated formulation comprises medium chain fatty acids or esters or coconut oil; at least one omega-3 fatty acid; an omega-6 fatty acid; at least one vitamin E isoform; and carnitine. For example, in some embodiments, a contemplated formulation comprises medium chain fatty acids or esters or coconut oil; EPA; DHA; GLA; alpha-tocopherol; gamma-tocopherol; and carnitine. In other embodiments, a contemplated formulation comprises medium chain fatty acids or esters or coconut oil; at least one omega-3 fatty acid; an omega-6 fatty acid; an omega-9 fatty acid; at least one vitamin E isoform; and carnitine. For example, in some embodiments, a contemplated formulation comprises medium chain fatty acids or esters or coconut oil; EPA; DHA; GLA; oleic acid; alpha-tocopherol; gamma-tocopherol; and carnitine.

In some embodiments, the carnitine component of a contemplated formulation is 90%-100% L-carnitine (or a salt thereof). In other embodiments, the carnitine component of a contemplated formulation is 90%-100% acetyl-carnitine. In other embodiments, the carnitine component of a contemplated formulation is a mixture of L-carnitine (or a salt thereof) and acetyl-carnitine. For example, in some embodiments, the carnitine component of a contemplated formulation can comprise 10% L-carnitine and 90% acetyl-carnitine; 15% L-carnitine and 85% acetyl-carnitine; 20% L-carnitine and 80% acetyl-carnitine; 25% L-carnitine and 75% acetyl-carnitine; 30% L-carnitine and 70% acetyl-carnitine; 40% L-carnitine and 60% acetyl-carnitine; 50% L-carnitine and 50% acetyl-carnitine; 60% L-carnitine and 40% acetyl-carnitine; 70% L-carnitine and 30% acetyl-carnitine; 75% L-carnitine and 25% acetyl-carnitine; 80% L-carnitine and 20% acetyl-carnitine; 85% L-carnitine and 15% acetyl-carnitine; or 90% L-carnitine and 10% acetyl-carnitine; or L-carnitine and acetyl-carnitine in any other proportion, where the percentages are by weight.

Probiotics

A "probiotic" is a bacterium wherein the bacterium typically confers a health benefit. *Lactobacillus* and *Bifidobacterium* are common probiotics. Examples of probiotics include *Lactobacillus rhamnosus, Lactobacillus plantarum, Lactobacillus casei, Lactobacillus acidophilus, Bifidobacterium infantis, Bifidobacterium animalis*, and *Escherichia coli* Nissle 1917, In some embodiments, a contemplated formulation comprises medium chain fatty acids or esters or coconut oil and a probiotic (e.g., *Lactobacillus rhamnosus*). Thus, e.g., in some embodiments, a contemplated formulation comprises medium chain fatty acids or esters or coconut oil; long chain fatty acid; at least one vitamin E isoform; and a probiotic. In some embodiments, a contemplated formulation comprises medium chain fatty acids or esters or coconut oil; at least one omega-3 fatty acid; at least one vitamin E isoform; and a probiotic. For example, in some embodiments, a contemplated formulation comprises medium chain fatty acids or esters or coconut oil; EPA; DHA; at least one vitamin E isoform; and a probiotic. In some embodiments, a contemplated formulation comprises medium chain fatty acids or esters or coconut oil; EPA; DHA; alpha-tocopherol; gamma-tocopherol; and a probiotic. In other embodiments, a contemplated formulation comprises medium chain fatty acids or esters or coconut oil; at least one omega-3 fatty acid; an omega-6 fatty acid; at least one vitamin E isoform; and a probiotic. For example, in some embodiments, a contemplated formulation comprises medium chain fatty acids or esters or coconut oil; EPA; DHA; GLA; alpha-tocopherol; gamma-tocopherol; and a probiotic. In other embodiments, a contemplated formulation comprises medium chain fatty acids or esters or coconut oil; at least one omega-3 fatty acid; an omega-6 fatty acid; an omega-9 fatty acid; at least one vitamin E isoform; and a probiotic. For example, in some embodiments, a contemplated formulation comprises medium chain fatty acids or esters or coconut oil; EPA; DHA; GLA; oleic acid; alpha-tocopherol; gamma-tocopherol; and a probiotic.

Amounts

The amounts in a contemplated formulation of medium chain fatty acids or esters or coconut oil; long chain fatty acids; and a vitamin E, as well as the amounts of additional components such as carnitine and alpha-lipoic acid, can vary according to various factors, including, e.g., the age of the individual, the weight of the individual, the genetic makeup of the individual, and the severity of symptoms exhibited by the individual to whom a formulation is administered. The following are general guidelines. Amounts are given as per unit dose.

Where a contemplated formulation includes medium chain fatty acids, or esters thereof, the medium chain fatty acids, or esters thereof are present in amount of from about 100 mg to about 5000 mg, e.g., from about 100 mg to about 200 mg, from about 200 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 mg to about 900 mg, from about 900 mg to about 1000 mg, from about 1000 mg to about 1100 mg, from about 1100 mg to about 1200 mg, from about 1200 mg to about 1300 mg, from about 1300 mg to about 1400 mg, from about 1400 mg to about 1500 mg, from about 1500 mg to about 1600 mg, from about 1600 mg to about 1700 mg, from about 1700 mg to about 1800 mg, from about 1800 mg to about 1900 mg, from about 1900 mg to about 2000 mg, from about 2000 mg to about 2500 mg, from about 2500 mg to about 3000 mg, from about 3000 mg to about 3500 mg, from about 3500 mg to about 4000 mg, from about 4000 mg to about 4500 mg, or from about 4500 mg to about 5000 mg per unit dose, where the amounts given are for individual comprising medium chain fatty acids, or esters thereof or for total comprising medium chain fatty acids, or esters thereof (e.g., where more than one comprising medium chain fatty acids, or esters thereof is present).

Where a contemplated formulation includes omega-3 fatty acids, the omega-3 fatty acids are present in amount of from about 100 mg to about 5000 mg, e.g., from about 100 mg to about 200 mg, from about 200 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 mg to about 900 mg, from about 900 mg to about 1000 mg, from about 1000 mg to about 1100 mg, from about 1100 mg to about 1200 mg, from about 1200 mg to about 1300 mg, from about 1300 mg to about 1400 mg, from about 1400 mg to about 1500 mg, from about 1500 mg to about 1600 mg, from about 1600 mg to about 1700 mg, from about 1700 mg to about 1800 mg, from about 1800 mg to about 1900 mg, from about 1900 mg to about 2000 mg, from about 2000 mg to about 2500 mg, from about 2500 mg to about 3000 mg, from about 3000 mg to about 3500 mg, from about 3500 mg to about 4000 mg, from about 4000 mg to about 4500 mg, or from about 4500 mg to about 5000 mg per unit dose, where the amounts given are for individual omega-3 fatty acids or for total omega-3 fatty acids (e.g., where more than one omega-3 fatty acid is present).

For example, in some embodiments, a contemplated formulation comprises the omega-3 fatty acids EPA and DHA. In some embodiments, a contemplated formulation will comprise EPA in an amount of from about 500 mg to about 3000 mg, e.g., from about 500 mg to about 600 mg, from about 600 mg to about 700 mg, from about 700 mg to about 800 mg, from about 800 mg to about 900 mg, from about 900 mg to about 1000 mg, from about 1000 mg to about 1500 mg, from about 1500 mg to about 2000 mg, from about 2000 mg to about 2500 mg, or from about 2500 mg to about 3000 mg per unit dose; and will comprise DHA in an amount of from about 100 mg to about 400 mg, e.g., from about 100 mg to about 150 mg, from about 150 mg to about 200 mg, from about 200 mg to about 250 mg, from about 250 mg to about 300 mg, from about 300 mg to about 350 mg, or from about 350 mg to about 400 mg per unit dose.

Where a contemplated formulation comprises the omega-3 fatty acids EPA and DHA, the ratio of EPA to DHA can range from about 1.5:1 (EPA:DHA) to about 5:1 (EPA:DHA), where the ratio is on a weight basis. For example, the EPA:DHA ratio can range from about 1.5:1 to about 2:1, from about 2:1 to about 2.5:1, from about 2.5:1 to about 3:1, from about 3:1 to about 3.5:1, from about 3.5:1 to about 4:1, from about 4:1 to about 4.5:1, or from about 4.5:1 to about 5:1. In some embodiments, a contemplated formulation comprises EPA and DHA in a ratio of 2.5:1 EPA:DHA.

The amount of vitamin E present in a subject formulation can be expressed in units (International Units, or IU), or in milligrams. In the past, the U.S. Dietary Reference Intake (DRI) Recommended Dietary Allowances (RDA) of vitamin E were expressed in Units. This "units" term has been replaced in recent years by alpha-tocopherol equivalents ("alpha-TE") or milligrams. One Unit is equivalent to 1 mg of dl-alpha-tocopherol acetate or 0.6 mg d-alpha-tocopherol. Throughout this specification, amounts of vitamin E are given in mg.

The alpha-tocopherol and gamma-tocopherol isoforms of vitamin E can be present in a contemplated formulation in an amount of from about 100 mg to about 10,000 mg, e.g., from about 100 mg to about 200 mg, from about 200 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 mg to about 900 mg, from about 900 mg to about 1000 mg, from about 1000 mg to about 2000 mg, from about 2000 mg to about 3000 mg, from about 3000 mg to about 3000 mg, from about 4000 mg to about 5000 mg, from about 5000 mg to about 6000 mg, from about 6000 mg to about 7000 mg, from about 7000 mg to about 8000 mg, from about 8000 mg to about 9000 mg, or from about 9000 mg to about 10,000 mg per unit dose, where the amounts given are for individual isoforms of vitamin E. In some embodiments, the alpha-tocopherol is d-alpha-tocopherol.

In some embodiments, a contemplated formulation includes alpha-tocopherol in an amount of from about 500 mg to about 3000 mg per unit dose, e.g., in an amount of from about 500 mg, from about 500 mg to about 600 mg, from about 600 mg to about 700 mg, from about 700 mg to about 800 mg, from about 800 mg to about 900 mg, from about 900 mg to about 1000 mg, from about 1000 mg to about 2000 mg, or from about 2000 mg to about 3000 mg per unit dose; and gamma-tocopherol in an amount of from about 200 mg to about 1000 mg per unit dose, e.g., in an amount of from about 200 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 mg to about 900 mg, or from about 900 mg to about 1000 mg per unit dose. In some of these embodiments, the formulation does not include vitamin E isoforms other than alpha-tocopherol and gamma-tocopherol. In other embodiments, the formulation includes, in addition to alpha-tocopherol and gamma-tocopherol, at least one additional vitamin E isoform.

In some embodiments, a contemplated formulation includes alpha-tocopherol and gamma-tocopherol; and does not include other vitamin E isoforms. In other embodiments, a contemplated formulation includes alpha-tocopherol and gamma-tocopherol; and one or more additional isoforms of vitamin E. Where a contemplated formulation includes alpha-tocopherol and gamma-tocopherol, the alpha-tocopherol can be present in an amount of from about 500 mg to about 10,000 mg, e.g., from about 500 mg to about 1000 mg, from about 1000 mg to about 2000 mg, from about 2000 mg to about 3000 mg, from about 3000 mg to about 3000 mg, from about 4000 mg to about 5000 mg, from about 5000 mg to about 6000 mg, from about 6000 mg to about 7000 mg, from about 7000 mg to about 8000 mg, from about 8000 mg to about 9000 mg, or from about 9000 mg to about 10,000 mg; and the gamma-tocopherol can be present in an amount of from about 100 mg to about 1000 mg, e.g., from about 100 mg to about 200 mg, from about 200 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 mg to about 900 mg, or from about 900 mg to about 1000 mg per unit dose.

Other forms of vitamin E (e.g., beta-tocopherol, delta-tocopherol, alpha-tocotrienol, beta-tocotrienol, delta-tocotrienol, and gamma-tocotrienol), if present in a contemplated formulation, can be present in an amount of from about 5 mg to about 2000 mg, e.g., from about 5 mg to about 10 mg, from about 10 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, or from about 175 mg to about 200 mg, from about 200 mg to about 250 mg, from about 250 mg to about 500 mg, from about 500 mg to about 750 mg, from about 750 mg to about 1000 mg, from about 1000 mg to about 1250 mg, from about 1250 mg to about 1500 mg, from about 1500 mg to about 1750 mg, or from about 1750 mg to about 2000 mg per unit dose, where the amounts given are for the individual isoforms of vitamin E.

Where a contemplated formulation comprises one or more omega-6 fatty acids, the omega-6 fatty acid can be present in the formulation in an amount of from about 50 mg to about 500 mg, e.g., from about 50 mg to about 75 mg, from about 75 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, or from about 450 mg to about 500 mg per unit dose.

Where a contemplated formulation comprises one or more omega-9 fatty acids, the omega-9 fatty acid can be present in a subject formulation in an amount of from about 50 mg to about 500 mg, e.g., from about 50 mg to about 75 mg, from about 75 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, or from about 450 mg to about 500 mg per unit dose.

Where a subject formulation comprises alpha-lipoic acid, the alpha-lipoic acid can be present in a subject formulation in an amount of from about 50 mg to about 1000 mg, e.g., from about 50 mg to about 75 mg, from about 75 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 600 mg, from about 600 mg to about 700 mg, from about 700 mg to about 800 mg, from about 800 mg to about 900 mg, or from about 900 mg to about 1000 mg per unit dose.

Where a subject formulation comprises carnitine, the carnitine can be present in a subject formulation in an amount of from about 150 mg to about 3000 mg, e.g., from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 600 mg, from about 600 mg to about 700 mg, from about 700 mg to about 800 mg, from about 800 mg to about 900 mg, from about 900 mg to about 1000 mg, from about 1000 mg to about 1250 mg, from about 1250 mg to about 1500 mg, from about 1500 mg to about 1750 mg, from about 1750 mg to about 2000 mg, from about 2000 mg to about 2250 mg, from about 2250 mg to about 2500 mg, from about 2500 mg to about 2750 mg, or from about 2750 mg to about 3000 mg per unit dose.

Additional Components

In certain embodiments, the disclosure relates to a dietary formulation comprising: a) medium chain fatty acid, glycerol ester, phospholipid ester, or alkyl ester thereof, b) an omega-3 fatty acid, alkyl ester thereof, or glycerol ester thereof, and c) a vitamin E isomer and additional components. In certain embodiments, the additional components are selected from long chain fatty acids, esters of long chain fatty acids, alpha-lipoic acid, carnitine, an omega-6 fatty acid, esters of omega-6 fatty acid, gamma-linolenic acid, ethyl gamma-linolenate, an omega-9 fatty acid, esters of omega-9 fatty acid, oleic acid, ethyl oleate, zinc, calcium, magnesium, selenium, a vitamin A, a vitamin $B_1$, a vitamin $B_2$, a vitamin $B_3$, a vitamin $B_5$, a vitamin $B_6$, a vitamin $B_7$, a vitamin $B_9$, a vitamin $B_{12}$, vitamin C, vitamin D, vitamin K, S-adenosylmethionine, a phosphocholine, creatine, a coenzyme Q, taurine, tetrahydrobiopterin, methylcobalamin, betaine, pancreatic enzymes, folinic acid, pancrelipase, a leukotriene inhibitor, a arginine, glutamine, N-acetylcysteine, an anti-fungal agent, berberine, an anti-inflammatory agent, anti-bacterial agent, anti-oxidant, saccharides and polysaccharides or combinations thereof.

In some embodiments, a contemplated formulation comprises medium chain fatty acids, or esters thereof; an omega 3 fatty acid or ester; at least one vitamin E isoform; and one, two, three, four, five, six, seven, eight, nine, ten, 11, 12, 13, 14, 15, 16, 17, 18, 19, or more or all of: long chain fatty acids, esters of long chain fatty acids, alpha-lipoic acid, carnitine, an omega-6 fatty acid, esters of omega-6 fatty acid, gamma-linolenic acid, ethyl gamma-linolenate, an omega-9 fatty acid, esters of omega-9 fatty acid, oleic acid, ethyl oleate, zinc, calcium, magnesium, selenium, a vitamin A, a vitamin $B_1$, a vitamin $B_2$, a vitamin $B_3$, a vitamin $B_5$, a vitamin $B_6$, a vitamin $B_7$, a vitamin $B_9$, a vitamin $B_{12}$, vitamin C, vitamin D, vitamin K, S-adenosylmethionine, a phosphocholine, creatine, a coenzyme Q, taurine, tetrahydrobiopterin, methylcobalamin, betaine, pancreatic enzymes, folinic acid, pancrelipase, a leukotriene inhibitor, a arginine, glutamine, N-acetylcysteine, an anti-fungal agent, berberine, an anti-inflammatory agent, anti-bacterial agent, anti-oxidant, saccharides and polysaccharides or combinations thereof.

In some embodiments, a contemplated formulation includes a contemplated formulation comprises medium chain fatty acids, or esters thereof; an omega 3 fatty acid or ester; a vitamin E; and one or more amino acids. In some embodiments, a contemplated formulation includes an anti-fungal agent (e.g., imidozoles and triazoles, nystatin, amphotericin B etc). In some embodiments, a contemplated formulation comprises medium chain fatty acids, or esters thereof; an omega 3 fatty acid or ester; a vitamin E; and an anti-inflammatory agent. In some embodiments, a contemplated formulation comprises medium chain fatty acids, or esters thereof; an omega 3 fatty acid or ester; a vitamin E; and an agent that reduces oxidative stress.

In some embodiments, a contemplated formulation comprises medium chain fatty acids, or esters thereof; an omega 3 fatty acid or ester; at least one vitamin E isoform; and a pancreatic enzyme. In some embodiments, a contemplated formulation comprises medium chain fatty acids, or esters thereof; an omega 3 fatty acid or ester; at least one vitamin E isoform; and a leukotriene inhibitor. In some embodiments, a contemplated formulation comprises medium chain fatty acids, or esters thereof; an omega 3 fatty acid or ester; at least one vitamin E isoform; and a mast cell stabilizer (e.g., cromolyn). In other embodiments, a contemplated formulation comprises medium chain fatty acids, or esters thereof; an omega 3 fatty acid or ester; at least one vitamin E isoform; a pancreatic enzyme; and a leukotriene inhibitor. For example, in some embodiments, a contemplated formulation comprising medium chain fatty acids, or esters thereof; an omega-3 fatty acid (e.g., EPA; DHA; or a combination of EPA and DHA, as described above; vitamin E (e.g., alpha-tocopherol and gamma-tocopherol); alpha-lipoic acid; carnitine; a pancreatic enzyme; and a leukotriene inhibitor.

Any minerals in a subject formulation can be present in salt form. Such salts can be carbonate, oxide, hydroxide, chloride, sulfate, phosphate, gluconate, lactate, acetate, fumarate, citrate, malate, amino acids, and the like for the cationic minerals and sodium, potassium, calcium, magnesium, and the like for the anionic minerals.

Zinc

In some embodiments, a contemplated formulation comprises medium chain fatty acids, or esters thereof; an omega 3 fatty acid or ester; at least one isoform of vitamin E; and zinc. In some embodiments, a contemplated formulation comprises medium chain fatty acids, or esters thereof; an omega 3 fatty acid or ester; at least one isoform of vitamin E; carnitine; and zinc. In other embodiments, a contemplated formulation comprises medium chain fatty acids, or esters thereof; an omega 3 fatty acid or ester; at least one isoform of vitamin E; alpha-lipoic acid; and zinc.

Zinc can be present in a subject formulation in the form of zinc gluconate, zinc sulfate, zinc chloride, or any salt of zinc. Zinc can be present in a subject formulation in an amount of from about 5 mg to about 50 mg, from about 5 mg to about 10 mg, from about 10 mg to about 15 mg, from about 15 mg to about 20 mg, from about 20 mg to about 25 mg, from about 25 mg to about 30 mg, from about 30 mg to about 40 mg, or from about 40 mg to about 50 mg total daily dose or per unit dose.

Calcium

In some embodiments, a contemplated formulation comprising medium chain fatty acids, or esters thereof; an omega 3 fatty acid or ester; at least one isoform of vitamin E; and calcium. In some embodiments, a contemplated formulation comprising medium chain fatty acids, or esters thereof; an omega 3 fatty acid or ester; at least one isoform of vitamin E; carnitine; and calcium. In other embodiments, a contemplated formulation comprising medium chain fatty acids, or esters thereof; an omega 3 fatty acid or ester; at least one isoform of vitamin E; alpha-lipoic acid; and calcium.

Calcium can be present in a subject formulation in the form of calcium carbonate, calcium citrate, calcium glubionate, calcium gluconate, calcium lactate, dibasic calcium phosphate, tribasic calcium phosphate, calcium acetate, and the like.

Calcium can be present in a subject formulation in an amount of from about 40 mg to about 2000 mg, from about 40 mg to about 100 mg, from about 100 mg to about 250 mg, from about 250 mg to about 500 mg, from about 500 mg to about 750 mg, from about 750 mg to about 1000 mg, from about 1000 mg to about 1500 mg, or from about 1500 mg to about 2000 mg total daily dose or per unit dose.

Magnesium

In some embodiments, a contemplated formulation comprising medium chain fatty acids, or esters thereof; an omega 3 fatty acid or ester; at least one isoform of vitamin E; and magnesium. In some embodiments, a contemplated formulation comprising medium chain fatty acids, or esters thereof; an omega 3 fatty acid or ester; at least one isoform of vitamin E; carnitine; and magnesium. In other embodiments, a contemplated formulation comprising medium chain fatty acids, or esters thereof; an omega 3 fatty acid or ester; at least one isoform of vitamin E; alpha-lipoic acid; and magnesium.

Magnesium can be present in a formulation as magnesium oxide, magnesium citrate, magnesium chloride, magnesium gluceptate, magnesium hydroxide, magnesium gluconate, magnesium lactate, magnesium pidolate, magnesium sulfate, and the like. Magnesium can be present in a subject formulation in an amount of from about 50 mg to about 1000 mg, from about 50 mg to about 75 mg, from about 75 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, or from about 400 mg to about 1000 mg total daily dose or per unit dose.

Selenium

In some embodiments, a contemplated formulation comprises medium chain fatty acids, or esters thereof; an omega 3 fatty acid or ester; at least one isoform of vitamin E; and selenium. In some embodiments, a contemplated formulation comprises medium chain fatty acids, or esters thereof; an omega 3 fatty acid or ester; at least one isoform of vitamin E; carnitine; and selenium. In other embodiments, a contemplated formulation comprises medium chain fatty acids, or esters thereof; an omega 3 fatty acid or ester; at least one isoform of vitamin E; alpha-lipoic acid; and selenium.

Selenium can be present in the form of sodium selenate, sodium selenite, selenomethionine, and the like. Selenium can be present in a subject formulation in an amount of from about 20 µg to about 500 µg, from about 20 µg to about 30 µg, from about 30 µg to about 40 µg, from about 40 µg to about 50 µg, from about 50 µg to about 75 µg, from about 75 µg to about 100 µg, from about 100 µg to about 150 µg, from about 150 µg to about 200 µg, from about 200 µg to about 250 µg, from about 250 µg to about 300 µg, from about 300 µg to about 350 µg, from about 350 µg to about 400 µg, or from about 400 µg to about 500 µg total daily or unit dose.

Vitamin A

In some embodiments, a contemplated formulation comprises medium chain fatty acids, or esters thereof; an omega 3 fatty acid or ester; at least one isoform of vitamin E; and a vitamin A. In some embodiments, a contemplated formulation comprises medium chain fatty acids, or esters thereof; an omega 3 fatty acid or ester; at least one isoform of a vitamin E; carnitine; and a vitamin A. In some embodiments, a contemplated formulation comprises medium chain fatty acids, or esters thereof; an omega 3 fatty acid or ester; at least one isoform of vitamin E; alpha-lipoic acid; and a vitamin A.

A "vitamin A" includes retinol, retinal (retinaldehyde), and retinoic acid; nor-retinoids; retro-retinoids; seco-retinoids (e.g., 1,6-seco-1,2-didehydroretinol); substituted retinoids (e.g., 5,6-Epoxy-5,6-dihydroretinol; ethyl 12-fluororetinoate; etc.); and analogs such as 3-hydroxyretinol, 3-hydroxyretinoic acid, 3-hydroxyretinal, 4-oxoretinol, 4-oxoretinoic acid, 4-oxoretinal, 3,4-didehydroretinol (vitamin $A_2$), 3,4-didehydroretinoic acid, 3,4-didehydroretinal, 4,5-didehydro-5,6-dihydroretinol, acycloretinol, acycloretinoic acid, and acycloretinal; and esters of vitamin A, e.g., an acetate ester, a succinate ester, a palmitate ester, etc.

A vitamin A can be present in a contemplated formulation in an amount of from about 200 IU to about 10,000 IU, e.g., 200 IU to about 250 IU, from about 250 IU to about 500 IU, from about 500 IU to about 1000 IU, from about 1000 IU to about 2000 IU, from about 2000 IU to about 3000 IU, from about 3000 IU to about 4000 IU, from about 4000 IU to about 5000 IU, from about 5000 IU to about 7500 IU, or from about 7500 IU to about 10,000 IU total daily dose.

Vitamin $B_1$

In some embodiments, a contemplated formulation comprises medium chain fatty acids, or esters thereof; an omega 3 fatty acid or ester; at least one isoform of vitamin E; and a vitamin $B_1$. In some embodiments, a contemplated formulation comprises medium chain fatty acids, or esters thereof; an omega 3 fatty acid or ester; at least one isoform of vitamin E; carnitine; and a vitamin $B_1$. In other embodiments, a contemplated formulation comprises medium chain fatty acids, or esters thereof; an omega 3 fatty acid or ester; at least one isoform of vitamin E; alpha-lipoic acid; and a vitamin $B_1$.

A "vitamin $B_1$" includes thiamine (also referred to as "thiamin"); the hydrochloride and nitrate salts of thiamine; and thiamine alkyl disulfides such as thiamine propyldisulfide, thiamine tetrahydrofurfuryl disulfide, and thiamine o-benzoyl disulfide; neopyrithiamine; oxyneopyrithiamine; and the like.

A vitamin $B_1$ can be present in a subject formulation in an amount of from about 0.05 mg to about 15 mg, from about 0.05 mg to about 0.1 mg, from about 0.1 mg to about 1.0 mg, from about 1.0 mg to about 1.5 mg, from about 1.5 mg to about 2.0 mg, from about 2.0 mg to about 2.5 mg, from about 2.5 mg to about 5 mg, from about 5 mg to about 7.5 mg, from about 7.5 mg to about 10 mg, from about 10 mg to about 12.5 mg, or from about 12.5 mg to about 15 mg total daily dose or per unit dose.

Vitamin $B_2$

In some embodiments, a contemplated formulation comprises medium chain fatty acids, or esters thereof; an omega 3 fatty acid or ester; at least one isoform of a vitamin E; and a vitamin $B_2$. In some embodiments, a contemplated formulation comprises medium chain fatty acids, or esters thereof; an omega 3 fatty acid or ester; at least one isoform of a vitamin E; carnitine; and a vitamin $B_2$. In other embodiments, a contemplated formulation comprises medium chain fatty acids, or esters thereof; an omega 3 fatty acid or ester; at least one isoform of a vitamin E; alpha-lipoic acid; and a vitamin $B_2$.

A "vitamin $B_2$" includes riboflavin; crystalline riboflavin coenzyme forms of riboflavin such as flavin adenine dinucleotide, flavin adenine mononucleotide, riboflavin 5-phosphate and their salts. Vitamin $B_2$ can be present in a subject formulation in an amount of from about 0.05 mg to about 15 mg, from about 0.05 mg to about 0.1 mg, from about 0.1 mg to about 1.0 mg, from about 1.0 mg to about 1.5 mg, from about 1.5 mg to about 2.0 mg, from about 2.0 mg to about 2.5 mg, from about 2.5 mg to about 5 mg, from about 5 mg to about 7.5 mg, from about 7.5 mg to about 10 mg, from about 10 mg to about 12.5 mg, or from about 12.5 mg to about 15 mg total daily dose or per unit dose.

Vitamin $B_3$

In some embodiments, a contemplated formulation comprises medium chain fatty acids, or esters thereof; an omega 3 fatty acid or ester; at least one isoform of vitamin E; and a vitamin B. In some embodiments, a contemplated formulation comprises medium chain fatty acids, or esters thereof; an omega 3 fatty acid or ester; at least one isoform of vitamin E; carnitine; and vitamin $B_3$. In other embodiments, a contemplated formulation comprises medium chain fatty acids, or esters thereof; an omega 3 fatty acid or ester; at least one isoform of vitamin E; alpha-lipoic acid; and vitamin $B_3$.

A "vitamin $B_3$" includes niacin, niacinamide, nicotinamide adenine dinucleotide, and nicotinamide adenine dinucleotide phosphate. A vitamin $B_3$ can be present in a subject formulation in an amount of from about 0.5 mg to about 200 mg, from about 0.5 mg to about 1 mg, from about 1 mg to about 10 mg, from about 10 mg to about 25 mg, from about 25 mg to about 50 mg, from about 50 mg to about 75 mg, from about 75 mg to about 100 mg, from about 100 mg to about 150 mg, or from about 150 mg to about 200 mg.

Vitamin $B_5$

In some embodiments, a contemplated formulation comprises medium chain fatty acids, or esters thereof; an omega 3 fatty acid or ester; at least one isoform of vitamin E; and a vitamin $B_5$. In some embodiments, a contemplated formulation comprises medium chain fatty acids, or esters thereof; an omega 3 fatty acid or ester; at least one isoform of vitamin E; carnitine; and vitamin $B_5$. In other embodiments, a contemplated formulation comprises medium chain fatty acids, or esters thereof; an omega 3 fatty acid or ester; at least one isoform of vitamin E; alpha-lipoic acid; and a vitamin $B_5$.

A "vitamin $B_5$" is also referred to as pantothenic acid, and encompasses salts such as calcium pantothenate; pantothenol; and panthenol. Vitamin $B_5$ can be present in a completed formulation in an amount of from about 0.4 mg to about 800 mg, from about 0.4 mg to about 1 mg, from about 1 mg to about 10 mg, from about 10 mg to about 25 mg, from about 25 mg to about 50 mg, from about 50 mg to about 100 mg, from about 100 mg to about 200 mg, from about 200 mg to about 300 mg, from about 300 mg to about 400 mg, from about 400 mg to about 500 mg, from about 500 mg to about 600 mg, from about 600 mg to about 700 mg, or from about 700 mg to about 800 mg total daily dose or per unit dose.

Vitamin $B_6$

In some embodiments, a contemplated formulation comprises medium chain fatty acids, or esters thereof; an omega 3 fatty acid or ester; at least one isoform of a vitamin E; and a vitamin $B_6$. In some embodiments, a contemplated formulation comprises medium chain fatty acids, or esters thereof; an omega 3 fatty acid or ester; at least one isoform of a vitamin E; carnitine; and a vitamin $B_6$. In other embodiments, a contemplated formulation comprises medium chain fatty acids, or esters thereof; an omega 3 fatty acid or ester; at least one isoform of a vitamin E; alpha-lipoic acid; and a vitamin $B_6$.

A "vitamin $B_6$" includes pyridoxine, pyridoxal, pyridoxamine; and hydrochloride salts or 5-phosphates of pyridoxine, pyridoxamine, or pyridoxal. For example, pyridoxine hydrochloride can be included in a contemplated formulation.

A vitamin $B_6$ can be present in a contemplated formulation in an amount of from about 2 mg to about 250 mg, from about 2 mg to about 5 mg, from about 5 mg to about 10 mg, from about 10 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, or from about 225 mg to about 250 mg total daily dose or per unit dose.

Vitamin $B_7$

In some embodiments, a contemplated formulation comprising medium chain fatty acids, or esters thereof; an omega 3 fatty acid or ester; at least one isoform of a vitamin E; and a vitamin $B_7$. In some embodiments, a contemplated formulation comprising medium chain fatty acids, or esters thereof; an omega 3 fatty acid or ester; at least one isoform of a vitamin E; a carnitine; and vitamin $B_7$. In other embodiments, a contemplated formulation comprising medium chain fatty acids, or esters thereof; an omega 3 fatty acid or ester; at least one isoform of vitamin E; alpha-lipoic acid; and vitamin $B_7$.

A "vitamin $B_7$" includes biotin, oxybiotin, biocytin, biotinol, D-homobiotin, D-norbiotin, dethiobiotin, biotin sulfone, biotin diamine sulfate, and the like. Vitamin $B_7$ can be present in a subject formulation in an amount of from about 10 μg to about 800 μg, from about 10 μg to about 25 μg, from about 25 μg to about 50 μg, from about 50 μg to about 100 μg, from about 100 μg to about 200 μg, from about 200 μg to about 300 μg, from about 300 μg to about 400 μg, from about 400 μg to about 500 μg, from about 500 μg to about 600 μg, from about 600 μg to about 700 μg, or from about 700 μg to about 800 μg total daily dose or per unit dose.

Vitamin $B_9$

In some embodiments, a contemplated formulation comprising medium chain fatty acids, or esters thereof; an omega 3 fatty acid or ester; at least one isoform of a vitamin E; and a vitamin $B_9$. In some embodiments, a contemplated formulation comprising medium chain fatty acids, or esters thereof; an omega 3 fatty acid or ester; at least one isoform of a vitamin E; carnitine; and a vitamin $B_9$. In other embodiments, a contemplated formulation comprising medium chain fatty acids, or esters thereof; an omega 3 fatty acid or ester; at least one isoform of vitamin E; alpha-lipoic acid; and a vitamin $B_9$.

A "vitamin $B_9$" (also known as pteroyl-L-glutamic acid; or folic acid) includes folic acid and any chemical derivative of folic acid that function equivalently to folic acid, such as mono and polyglutamyl folates, dihydro and tetrahydro folates, methyl and formyl folates, and any isomer of a folate, e.g., an isomer of a reduced folate. Thus, e.g., "folic acid" includes dihydrofolic acid, tetrahydrofolic acid, 5-formyltetrahydrofolic acid, 10-formyltetrahydrofolic acid, 5-10 methylenetetrahydrofolic acid, 5-10 methenyltetrahydrofolic acid, 5-methyltetrahydrofolic acid, and derivatives of any of the foregoing; and a natural isomer of reduced folate, such as (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and polyglutamyl derivatives of any of the foregoing. Derivatives of folic acid include the precursors (pro-vitamins), metabolites, derivatives, and conjugates of the parent compound, any of which may be either naturally occurring or synthetic; as well as the salts of the compounds.

A vitamin $B_9$ can be present in a subject formulation in an amount of from about 200 μg to about 1000 μg, e.g., from about 200 μg to about 400 μg, from about 400 μg to about 500 μg, from about 500 μg to about 600 μg, from about 600 μg to about 700 μg, from about 700 μg to about 800 μg, from about 800 μg to about 900 μg, or from about 900 μg to about 1000 μg total daily dose or per unit dose.

Vitamin $B_{12}$

In some embodiments, a contemplated formulation comprising medium chain fatty acids, or esters thereof; an omega 3 fatty acid or ester; at least one isoform of a vitamin E; and a vitamin $B_{12}$. In some embodiments, a contemplated formulation comprising medium chain fatty acids, or esters thereof; an omega 3 fatty acid or ester; at least one isoform of a vitamin E; carnitine; and a vitamin $B_{12}$. In other embodiments, a contemplated formulation comprising medium chain fatty acids, or esters thereof; an omega 3 fatty acid or ester; at least one isoform of a vitamin E; alpha-lipoic acid; and a vitamin $B_{12}$.

A "vitamin $B_{12}$" refers to vitamin $B_{12}$ (cyanocobalamin) and its pharmaceutical derivatives, such as methylcobalamin, hydroxocobalamin, cyano-10-chlorocobalamin, aquocobalamin perchlorate, aquo-10-chlorocobalamin perchlorate, azidocobalamin, chlorocobalamin, cobalamin, methylcobalamin, adenosylcobalamin, and hydroxocobalamin.

A vitamin $B_{12}$ can be present in a contemplated formulation in an amount of from about 2 μg to about 1000 μg, 2 μg to about 10 μg, from about 10 μg to about 25 μg, from about 25 μg to about 50 μg, from about 50 μg to about 100 μg, from about 100 μg to about 200 μg, from about 200 μg to about 300 μg, from about 300 μg to about 400 μg, from about 400 μg to about 500 μg, from about 500 μg to about 600 μg, from about 600 μg to about 700 μg, from about 700 μg to about 800 μg, from about 800 μg to about 900 μg, or from about 900 μg to about 1000 μg total daily dose or per unit dose.

Vitamin C

In some embodiments, a contemplated formulation comprising medium chain fatty acids, or esters thereof; long chain fatty acid or ester; (e.g., an omega-3 fatty acid or ester and/or an omega-6 fatty acid or ester); at least one isoform of a vitamin E; and a vitamin C. In some embodiments, a contemplated formulation comprises medium chain fatty acids, or esters thereof; an omega 3 fatty acid or ester; at least one isoform of a vitamin E; carnitine; and a vitamin C. In other embodiments, a contemplated formulation comprises medium chain fatty acids, or esters thereof; an omega 3 fatty acid or ester; at least one isoform of a vitamin E; alpha-lipoic acid; and a vitamin C.

A "vitamin C" includes all forms of ascorbic acid, such as L-ascorbic acid, D-ascorbic acid, DL-ascorbic acid, D-araboascorbic acid, dehydroascorbic acid, xyloascorbic acid, esters of ascorbic acid, salts of ascorbic acid, and the like.

A vitamin C can be present in a subject formulation in an amount of from about 80 mg to about 1000 mg, from about 80 mg to about 100 mg, from about 100 mg to about 200 mg, from about 200 mg to about 250 mg, from about 250 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 mg to about 900 mg, or from about 900 to about 1000 mg total daily dose or per unit dose.

Vitamin D

In some embodiments, a contemplated formulation comprising medium chain fatty acids, or esters thereof; an omega 3 fatty acid or ester; at least one isoform of a vitamin E; and a vitamin D. In some embodiments, a contemplated formulation comprising medium chain fatty acids, or esters thereof; an omega 3 fatty acid or ester; at least one isoform of a vitamin E; carnitine; and a vitamin D. In other embodiments, a contemplated formulation comprising medium chain fatty acids, or esters thereof; an omega 3 fatty acid or ester; at least one isoform of a vitamin E; alpha-lipoic acid; and a vitamin D.

A "vitamin D" includes, e.g., cholecalciferol (D3), ergocalciferol (D2), and biologically active metabolites and precursors such as, e.g., 1-alpha-hydroxy Vitamin D, 25-hydroxy Vitamin D, 1,25-dihydroxy Vitamin D, and the like.

A vitamin D can be present in a subject formulation in an amount of from about 200 mg to about 2000 mg, 200 IU to about 2000 IU, from about 200 IU to about 300 IU, from about 300 IU to about 400 IU, from about 400 IU to about 500 IU, from about 500 IU to about 600 IU, from about 600 IU to about 700 IU, or from about 700 IU to about 2000 IU total daily dose or per unit dose.

Vitamin K

In some embodiments, a contemplated formulation comprises medium chain fatty acids, or esters thereof; an omega 3 fatty acid or ester; at least one isoform of a vitamin E; and a vitamin K. In some embodiments, a contemplated formulation comprises medium chain fatty acids, or esters thereof; an omega 3 fatty acid or ester; at least one isoform of a vitamin E; carnitine; and a vitamin K. In other embodiments, a contemplated formulation comprises medium chain fatty acids, or esters thereof; an omega 3 fatty acid or ester; at least one isoform of vitamin E; alpha-lipoic acid; and a vitamin K.

In certain embodiments, the disclosure relates to a dietary formulation comprising: a) medium chain fatty acid, glycerol ester, or alkyl ester thereof, b) an omega-3 fatty acid, alkyl ester thereof, or glycerol ester thereof, c) a vitamin E isomer and d) a Vitamin K.

In certain embodiments, the disclosure relates to a dietary formulation comprising medium chain fatty acid, glycerol ester, or alkyl ester thereof, eicosapentaenoic acid, docosahexaenoic acid, alpha tocopherol, gamma tocopherol, vitamin K, and gamma-linolenic acid.

A "vitamin K" includes vitamin $K_1$ (phytonadione); Vitamin $K_2$ (menaquinones, e.g., menaquinone-4, menaquinone-7, etc.); Vitamin $K_3$ (menadione; or 2-methyl-1,4-naphthoquinone); a salt of a vitamin K; and a derivative of a vitamin K. In some embodiments, a contemplated formulation includes vitamin $K_1$. In other embodiments, a contemplated formulation includes vitamin $K_2$. In other embodiments, a contemplated formulation includes vitamin $K_1$ and vitamin $K_2$.

Vitamin $K_1$ can be present in a subject formulation in an amount of from about 100 µg to about 10 mg (total daily dose), e.g., from about 100 µg to about 500 µg, from about 500 µg to about 1 mg, from about 1 mg to about 2.5 mg, from about 2.5 mg to about 5 mg, from about 5 mg to about 7.5 mg, or from about 7.5 mg to about 10 mg.

Vitamin $K_2$ can be present in a subject formulation in an amount of from about 100 µg to about 2 mg (total daily dose), e.g., from about 100 µg to about 250 µg, from about 250 µg to about 500 µg, from about 500 µg to about 750 µg, from about 750 µg to about 1 mg, from about 1 mg to about 1.25 mg, from about 1.25 mg to about 1.5 mg, from about 1.5 mg to about 1.75 mg, or from about 1.75 mg to about 2 mg.

S-adenosylmethionine (SAMe)

In some embodiments, a contemplated formulation comprises medium chain fatty acids, or esters thereof; an omega 3 fatty acid or ester; at least one isoform of a vitamin E; and S-adenosylmethionine. In some embodiments, a contemplated formulation comprises medium chain fatty acids, or esters thereof; an omega 3 fatty acid or ester; at least one isoform of vitamin E; carnitine; and S-adenosylmethionine. In some embodiments, a contemplated formulation comprises medium chain fatty acids, or esters thereof; an omega 3 fatty acid or ester; at least one isoform of a vitamin E; alpha-lipoic acid; and S-adenosylmethionine. In some embodiments, a contemplated formulation comprises medium chain fatty acids, or esters thereof; an omega 3 fatty acid or ester; at least one isoform of a vitamin E; vitamin $B_9$; and S-adenosylmethionine. In some embodiments, a contemplated formulation comprises medium chain fatty acids, or esters thereof; an omega 3 fatty acid or ester; at least one isoform of a vitamin E; vitamin $B_{12}$; and S-adenosylmethionine. In some embodiments, a contemplated formulation comprises medium chain fatty acids, or esters thereof; an omega 3 fatty acid or ester; at least one isoform of a vitamin E; vitamin $B_9$; vitamin $B_{12}$, and S-adenosylmethionine.

"S-adenosylmethionine" includes 2-Amino-4-[[5-(6-aminopurin-9-yl)-3,4-dihydroxyoxolan-2-yl]methyl-methyl-sulfonio]butanoate and salts thereof. S-adenosylmethionine can be present in a subject formulation in an amount of from about 50 mg to about 5000 mg, e.g., from about 100 mg to about 1000 mg, from about 300 mg to about 2000 mg, from about 500 mg to about 3000 mg, from about 1000 mg to about 4000 mg, or from about 400 mg to about 500 mg total daily dose or per unit dose.

Phosphocholine

In some embodiments, a contemplated formulation comprises medium chain fatty acids, or esters thereof; an omega 3 fatty acid or ester; at least one isoform of a vitamin E; and a phosphocholine. In some embodiments, a contemplated formulation comprises medium chain fatty acids, or esters thereof; an omega 3 fatty acid or ester; at least one isoform of vitamin E; carnitine; and a phosphocholine. In some embodiments, a contemplated formulation comprises medium chain fatty acids, or esters thereof; an omega 3 fatty acid or ester; at least one isoform of a vitamin E; alpha-lipoic acid; and a phosphocholine.

A "phosphocholine" includes phosphatidylcholine derivatives of phosphocholine, e.g., polyenylphosphatidylcholine. A phosphocholine (or a phosphatidylcholine such as polyenylphosphatidylcholine) can be present in a subject formulation in an amount of from about 500 mg to about 5000 mg, e.g., from about 500 mg to about 1000 mg, from about 1000 mg to about 2000 mg, from about 2000 mg to about 3000 mg, from about 3000 mg to about 4000 mg, or from about 400 mg to about 5000 mg total daily dose or per unit dose.

Coenzyme Q

In some embodiments, a contemplated formulation comprises medium chain fatty acids, or esters thereof; an omega 3 fatty acid or ester; at least one isoform of a vitamin E; and a coenzyme Q. In some embodiments, a contemplated formulation comprises medium chain fatty acids, or esters thereof; an omega 3 fatty acid or ester; at least one isoform of a vitamin E; carnitine; and a coenzyme Q. In other embodiments, a contemplated formulation comprises medium chain fatty acids, or esters thereof; an omega 3 fatty acid or ester; at least one isoform of a vitamin E; alpha-lipoic acid; and a coenzyme Q.

A "coenzyme Q" (CoQ; 2,3-dimethoxy-5-methyl-6-polyprenyl-1,4-benzoquinone; also known as ubiquinone) refers to a group of lipid soluble benzoquinones involved in electron transport in mitochondrial preparations, e.g., in the oxidation of succinate or reduced nicotine adenine dinucleotide (NADH) via the cytochrome system. CoQ includes $CoQ_n$, where n is an integer from 1 to 12, and where n indicates the number of isoprenoid units. CoQ includes, e.g., $CoQ_{7-10}$, i.e. $CoQ_7$ (ubiquinone-7), $CoQ_9$ (ubiquinone-9), $CoQ_{10}$ (ubidecarenone), and mixtures of the foregoing. In some embodiments, the CoQ is ubidecarenone.

A CoQ can be present in a contemplated formulation in an amount of from about 4 mg to about 500 mg, from about 4 mg to about 10 mg, from about 10 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 200 mg, or from about 200 mg to about 500 mg total daily dose or per unit dose.

Creatine

In some embodiments, a contemplated formulation comprises medium chain fatty acids, or esters thereof; an omega 3 fatty acid or ester; at least one isoform of vitamin E; and creatine. In some embodiments, a contemplated formulation comprises medium chain fatty acids, or esters thereof; an omega 3 fatty acid or ester; at least one isoform of vitamin E; carnitine; and creatine. In other embodiments, a contemplated formulation comprises medium chain fatty acids, or esters thereof; an omega 3 fatty acid or ester; at least one isoform of vitamin E; alpha-lipoic acid; and creatine. In other embodiments, a contemplated formulation comprises medium chain fatty acids, or esters thereof; an omega 3 fatty acid or ester; at least one isoform of vitamin E; alpha-lipoic acid; arginine; and creatine. In other embodiments, a contemplated formulation comprises medium chain fatty acids, or esters thereof; an omega 3 fatty acid or ester; at least one isoform of vitamin E; alpha-lipoic acid; carnitine; and creatine. In other embodiments, a contemplated formulation comprises medium chain fatty acids, or esters thereof; an omega 3 fatty acid or ester; at least one isoform of vitamin E; alpha-lipoic acid; arginine; carnitine; and creatine.

"Creatine" includes 2-[Carbamimidoyl(methyl)amino]acetic acid and salts thereof. Creatine can be present in a subject formulation in an amount of from about 100 mg to about 30 g, from about 200 mg to about 20 g, from about 500 mg to about 10 g, from about 1000 mg to about 5 g, from about 1000 mg to about 3 g.

Taurine

In some embodiments, a contemplated formulation comprises medium chain fatty acids, or esters thereof; an omega 3 fatty acid or ester; at least one isoform of vitamin E; and taurine. In some embodiments, a contemplated formulation comprises medium chain fatty acids, or esters thereof; an omega 3 fatty acid or ester; at least one isoform of vitamin E; carnitine; and taurine. In other embodiments, a contemplated formulation comprises medium chain fatty acids, or esters thereof; an omega 3 fatty acid or ester; at least one isoform of vitamin E; alpha-lipoic acid; and taurine. In other embodiments, a contemplated formulation comprises medium chain fatty acids, or esters thereof; an omega 3 fatty acid or ester; at least one isoform of vitamin E; alpha-lipoic acid; arginine; and taurine. In other embodiments, a contemplated formulation comprises medium chain fatty acids, or esters thereof; an omega 3 fatty acid or ester; at least one isoform of vitamin E; alpha-lipoic acid; carnitine; and taurine. In other embodiments, a contemplated formulation comprises medium chain fatty acids, or esters thereof; an omega 3 fatty acid or ester; at least one isoform of vitamin E; alpha-lipoic acid; arginine; carnitine; and taurine.

"Taurine" includes 2-aminoethanesulfonic acid and salts thereof. Taurine can be present in a subject formulation in an amount of from about 20 mg to about 3000 mg, from about 20 mg to about 50 mg, from about 50 mg to about 100 mg, from about 100 mg to about 250 mg, from about 250 mg to about 500 mg, from about 500 mg to about 750 mg, from about 750 mg to about 1000 mg, from about 1000 mg to about 1500 mg, from about 1500 mg to about 2000 mg, from about 2000 mg to about 2500 mg, or from about 2500 mg to about 3000 mg.

Berberine

In some embodiments, a contemplated formulation comprises medium chain fatty acids, or esters thereof; an omega 3 fatty acid or ester; at least one isoform of vitamin E; and berberine. In some embodiments, a contemplated formulation comprises medium chain fatty acids, or esters thereof; an omega 3 fatty acid or ester; at least one isoform of vitamin E; carnitine; and berberine. In other embodiments, a contemplated formulation comprises medium chain fatty acids, or esters thereof; an omega 3 fatty acid or ester; at least one isoform of vitamin E; alpha-lipoic acid; and berberine. In other embodiments, a contemplated formulation comprises medium chain fatty acids, or esters thereof; an omega 3 fatty acid or ester; at least one isoform of vitamin E; alpha-lipoic acid; arginine; and berberine. In other embodiments, a contemplated formulation comprises medium chain fatty acids, or esters thereof; an omega 3 fatty acid or ester; at least one isoform of vitamin E; alpha-lipoic acid; carnitine; and berberine. In other embodiments, a contemplated formulation comprises medium chain fatty acids, or esters thereof; an omega 3 fatty acid or ester; at least one isoform of vitamin E; alpha-lipoic acid; arginine; carnitine; and berberine.

"Berberine" includes the compound 5,6-dihydro-9,10-dimethoxybenzo[g]-1,3-benzodioxolo[5,6-a]quinolizinium and salts thereof. In certain embodiments, berberine may be substituted with other like compounds such as sanguinarine, coptisine, goldenseal, and jatrorrhizine. In certain embodiments, berberine can be present in a subject formulation in an amount of from about 100 mg to about 2,000 mg, from about 200 mg to about 1,500 mg, from about 500 mg to about 1,500 mg.

Tetrahydrobiopterin

In some embodiments, a contemplated formulation comprises medium chain fatty acids, or esters thereof; an omega 3 fatty acid or ester; at least one isoform of vitamin E; and tetrahydrobiopterin. In some embodiments, a contemplated formulation comprises medium chain fatty acids, or esters thereof; an omega 3 fatty acid or ester; at least one isoform of vitamin E; carnitine; and tetrahydrobiopterin. In other embodiments, a contemplated formulation comprises medium chain fatty acids, or esters thereof; an omega 3 fatty acid or ester; at least one isoform of vitamin E; alpha-lipoic acid; and tetrahydrobiopterin. In other embodiments, a contemplated formulation comprises medium chain fatty acids, or esters thereof; an omega 3 fatty acid or ester; at least one isoform of vitamin E; alpha-lipoic acid; arginine; and tetrahydrobiopterin. In other embodiments, a contemplated formulation comprises medium chain fatty acids, or esters thereof; an omega 3 fatty acid or ester; at least one isoform of vitamin E; alpha-lipoic acid; carnitine; and tetrahydrobiopterin. In other embodiments, a contemplated formulation comprises medium chain fatty acids, or esters thereof; an omega 3 fatty acid or ester; at least one isoform of vitamin E; alpha-lipoic acid; arginine; carnitine; and tetrahydrobiopterin.

"Tetrahydrobiopterin" includes 5,6,7,8-tetrahydrobiopterin and salts thereof; L-erythro-5,6,7,8-tetrahydrobiopterin and salts thereof; and the like. Tetrahydrobiopterin can be present in a subject formulation in an amount of from about 20 mg to about 3000 mg, from about 20 mg to about 50 mg, from about 50 mg to about 100 mg, from about 100 mg to about 250 mg, from about 250 mg to about 500 mg, from about 500 mg to about 750 mg, from about 750 mg to about 1000 mg, from about 1000 mg to about 1500 mg, from about 1500 mg to about 2000 mg, from about 2000 mg to about 2500 mg, or from about 2500 mg to about 3000 mg.

Betaine

In some embodiments, a contemplated formulation comprises medium chain fatty acids, or esters thereof; an omega 3 fatty acid or ester; at least one isoform of vitamin E; and betaine. In some embodiments, a contemplated formulation comprises medium chain fatty acids, or esters thereof; an omega 3 fatty acid or ester; at least one isoform of vitamin E; betaine; and pepsin. In some embodiments, a contemplated formulation comprises medium chain fatty acids, or esters thereof; an omega 3 fatty acid or ester; at least one isoform of vitamin E; carnitine; and betaine. In other embodiments, a contemplated formulation comprises medium chain fatty acids, or esters thereof; an omega 3 fatty acid or ester; at least one isoform of vitamin E; alpha-lipoic acid; and betaine. In other embodiments, a contemplated formulation comprises medium chain fatty acids, or esters thereof; an omega 3 fatty acid or ester; at least one isoform of vitamin E; alpha-lipoic acid; arginine; and betaine. In other embodiments, a contemplated formulation comprises medium chain fatty acids, or esters thereof; an omega 3 fatty acid or ester; at least one isoform of vitamin E; alpha-lipoic acid; carnitine; and betaine. In other embodiments, a contemplated formulation comprises medium chain fatty acids, or esters thereof; an omega 3 fatty acid or ester; at least one isoform of vitamin E; alpha-lipoic acid; arginine; carnitine; and betaine.

"Betaine" includes trimethylglycine and salts thereof and the like. Betaine can be present in a subject formulation in an amount of from about 20 mg to about 3000 mg, from about 20 mg to about 50 mg, from about 50 mg to about 100 mg, from about 100 mg to about 250 mg, from about 250 mg to about 500 mg, from about 500 mg to about 750 mg, from about 750 mg to about 1000 mg, from about 1000 mg to about 1500 mg, from about 1500 mg to about 2000 mg, from about 2000 mg to about 2500 mg, or from about 2500 mg to about 3000 mg.

Pancreatic Enzymes

In some embodiments, a contemplated formulation comprises medium chain fatty acids, or esters thereof; an omega 3 fatty acid or ester; at least one isoform of vitamin E; and a pancreatic enzyme. Pancreatic enzymes include proteases, lipases, amylases, and nucleases. The term "pancreatic enzyme," as used herein, refers to any enzyme that provides a function (catalytic activity) of an enzyme produced by a human pancreas. For example, "pancreatic lipase" refers to any enzyme that provides a function of a lipase produced by a human pancreas.

In some embodiments, a contemplated formulation includes a lipase, e.g., a pancreatic lipase. In other embodiments, a subject formulation includes a pancreatic protease (e.g., trypsin, trypsinogen, chymotrypsin, chymotrypsinogen), and a pancreatic lipase. In other embodiments, a subject formation includes a pancreatic protease, a pancreatic lipase, and a pancreatic amylase.

In some embodiments, the enzyme is an inactive proenzyme (e.g., trypsinogen, chymotrysinogen). A pancreatic enzyme to be included in a formulation can be a naturally-occurring enzyme, a recombinant enzyme, or a synthetic enzyme; and can be from any of a variety of sources, e.g., a mammal, a fungus, a plant, etc. For example, fungal enzymes, and formulations comprising same, are described in, e.g., U.S. Pat. No. 6,051,220. In some embodiments, the enzyme is acid stable, e.g., is stable at a pH range of from about 2.8 to about 9. In some embodiments, the enzyme is in a microencapsulated and enteric coated formulation. Examples of such formulations include, e.g., Cotazym-S, Creon, Pancrease, Pancrease MT-16, Ultrase MT-20, and Zymase. Other suitable formulations include, e.g., a formulation as described in U.S. Pat. No. 5,750,104.

The amount of pancreatic enzyme present in a subject formulation can vary, according to need, and can be in a range of from about 2000 International Units (IU) to 40,000 IU per unit dose, e.g., from about 2000 IU to about 5000 IU, from about 5000 IU to about 7,500 IU, from about 7,500 IU to about 10,000 IU, from about 10,000 IU to about 15,000 IU, from about 15,000 IU to about 20,000 IU, from about 20,000 IU to about 30,000 IU, or from about 30,000 IU to about 40,000 IU per unit dose.

Leukotriene Inhibitors

In some embodiments, a contemplated formulation comprises medium chain fatty acids, or esters thereof; an omega 3 fatty acid or ester; at least one isoform of vitamin E; and a leukotriene inhibitor. Suitable leukotriene inhibitors include leukotriene receptor antagonists and leukotriene synthesis inhibitors. Exemplary leukotriene receptor antagonists include, e.g., zafirlukast (Accolate), montelukast (Singulair), pranlukast, iralukast, pobilukast and SKB-106,203. Leukotriene synthesis inhibitors include inhibitors of 5-lipoxygenase activity, where an exemplary 5-lipoxygenase inhibitor is zileuton (Zyflo). Suitable 5-lipoxygenase inhibitors include those described in, e.g., U.S. Pat. Nos. 5,364,877, 5,302,603, 5,234,950, 5,098,932 and 5,354,865. In some embodiments, a 5-lipoxygenase inhibitor also inhibits cyclooxygenase-2. In other embodiments, a 5-lipoxygenase inhibitor is a selective 5-lipoxygenase inhibitor, e.g., the inhibitor does not substantially inhibit enzymes other than 5-lipoxygenase, e.g., the inhibitor does not substantially inhibit a cyclooxygenase.

The amount of a leukotriene inhibitor that is included in a subject formulation can vary, depending on factors such as the age and/or weight of the individual to whom the formulation is administered, the severity of symptoms, etc. The amount of a leukotriene inhibitor that is included in a subject formulation can range from about 2 mg to about 100 mg, e.g., from about 2 mg to about 5 mg, from about 5 mg to about 10 mg, from about 10 mg to about 20 mg, from about 20 mg to about 30 mg, from about 30 mg to about 40 mg, from about 40 mg to about 50 mg, from about 50 mg to about 60 mg, from about 60 mg to about 70 mg, from about 70 mg to about 80 mg, from about 80 mg to about 90 mg, or from about 90 mg to about 100 mg per unit dose.

Amino Acids

In some embodiments, a contemplated formulation comprises medium chain fatty acids, or esters thereof; an omega 3 fatty acid or ester; at least one isoform of vitamin E; and one or more amino acids. For example, in some embodiments, a subject formulation includes arginine, glutamine, N-acetylcysteine, or both arginine and glutamine, or both arginine and N-acetylcysteine, or both glutamine and N-acetylcysteine. If arginine and/or glutamine and/or N-acetylcysteine is present in a formulation, the arginine and/or glutamine and/or N-acetylcysteine is present in an amount of from about 50 mg to about 10 g per unit dose, e.g., from about 100 mg to about 750 mg, from about 750 mg to about 1 g, from about 1 g to about 2.5 g, from about 2.5 g to about 5 g, from about 5 g to about 7.5 g, or from about 7.5 g to about 10 g. For example, a contemplated formulation comprises medium chain fatty acids, or esters thereof; an omega 3 fatty acid or ester; at least one isoform of vitamin E; and glutamine, the glutamine is present in an amount of from about 50 mg to about 10 g per unit dose, e.g., from about 100 mg to about 750 mg, from about 750 mg to about 1 g, from about 1 g to about 2.5 g, from about 2.5 g to about 5 g, from about 5 g to about 7.5 g, or from about 7.5 g to about 10 g.

As another example, where a contemplated formulation comprises medium chain fatty acids, or esters thereof; an omega 3 fatty acid or ester; at least one isoform of vitamin E; and arginine, the arginine is present in an amount of from about 50 mg to about 10 g per unit dose, e.g., from about 100 mg to about 750 mg, from about 750 mg to about 1 g, from about 1 g to about 2.5 g, from about 2.5 g to about 5 g, from about 5 g to about 7.5 g, or from about 7.5 g to about 10 g.

As another example, where a contemplated formulation comprises medium chain fatty acids, or esters thereof; an omega 3 fatty acid or ester; at least one isoform of vitamin E; and N-acetylcysteine, the N-acetylcysteine is present in an amount of from about 50 mg to about 10 g per unit dose, e.g., from about 100 mg to about 750 mg, from about 750 mg to about 1 g, from about 1 g to about 2.5 g, from about 2.5 g to about 5 g, from about 5 g to about 7.5 g, or from about 7.5 g to about 10 g.

As another example, where a contemplated formulation comprises medium chain fatty acids, or esters thereof; an omega 3 fatty acid or ester; at least one isoform of vitamin E; and both arginine, glutamine, and n-acetylcysteine, the arginine and glutamine and n-acetylcysteine are each present in an amount of from about 50 mg to about 10 g per unit dose, e.g., from about 100 mg to about 750 mg, from about 750 mg to about 1 g, from about 1 g to about 2.5 g, from about 2.5 g to about 5 g, from about 5 g to about 7.5 g, or from about 7.5 g to about 10 g.

Anti-Fungal Agents

In some embodiments, a contemplated formulation comprises medium chain fatty acids, or esters thereof; an omega 3 fatty acid or ester; at least one isoform of vitamin E; and an anti-fungal agent. Suitable anti-fungal agents include, but are not limited to, berberine, nystatin, amphotericin B, clotrimazole, flucytosine, fluconazole, itraconazole, ketoconazole, and noxafil. Where the anti-fungal agent is nystatin, the nystatin can be present in a subject formulation in an amount of from about 100,000 Units (U) to about 800,000 Upper unit dose, e.g., from about 100,000 U to about 200,000 U, from about 200,000 U to about 400,000 U, from about 400,000 U to about 600,000 U, or from about 600,000 U to about 800,000 Upper unit dose. In some embodiments, a contemplated formulation comprises medium chain fatty acids, or esters thereof; an omega 3 fatty acid or ester; at least one isoform of vitamin E; (e.g., alpha-tocopherol and gamma-tocopherol), carnitine, and nystatin.

In some embodiments, a contemplated formulation comprises medium chain fatty acids, or esters thereof; an omega 3 fatty acid or ester; at least one isoform of vitamin E; and berberine. In some embodiments, a contemplated formulation comprises medium chain fatty acids, or esters thereof; an omega 3 fatty acid or ester; at least one isoform of vitamin E; carnitine; and berberine. In other embodiments, a contemplated formulation comprises medium chain fatty acids, or esters thereof; an omega 3 fatty acid or ester; at least one isoform of vitamin E; alpha-lipoic acid; and berberine. In other embodiments, a contemplated formulation comprises medium chain fatty acids, or esters thereof; an omega 3 fatty acid or ester; at least one isoform of vitamin E; alpha-lipoic acid; arginine; and berberine. In other embodiments, a contemplated formulation comprises medium chain fatty acids, or esters thereof; an omega 3 fatty acid or ester; at least one isoform of vitamin E; alpha-lipoic acid; carnitine; and berberine. In other embodiments, a contemplated formulation comprises medium chain fatty acids, or esters thereof; an omega 3 fatty acid or ester; at least one isoform of vitamin E; alpha-lipoic acid; arginine; carnitine; and berberine.

"Berberine" includes 5,6-dihydro-9,10-dimethoxybenzo[g]-1,3-benzodioxolo[5,6-a]quinolizinium and salts thereof and the like. Berberine can be present in a subject formulation in an amount of from about 20 mg to about 3000 mg, from about 20 mg to about 100 mg, from about 50 mg to about 200 mg, from about 100 mg to about 250 mg, from about 250 mg to about 500 mg, from about 500 mg to about 750 mg, from about 750 mg to about 1000 mg, from about 1000 mg to about 1500 mg, from about 1500 mg to about 2000 mg, from about 2000 mg to about 2500 mg, or from about 2500 mg to about 3000 mg.

Anti-Inflammatory Agents

In some embodiments, a contemplated formulation comprises medium chain fatty acids, or esters thereof; an omega 3 fatty acid or ester; at least one isoform of vitamin E; and an anti-inflammatory agent. Suitable anti-inflammatory agents include, but are not limited to, steroidal anti-inflammatory agents, and non-steroidal anti-inflammatory agents. Suitable steroidal anti-inflammatory agents include, but are not limited to, hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, conisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures of two or more of the foregoing.

Suitable non-steroidal anti-inflammatory agents, include, but are not limited to, 1) the oxicams, such as piroxicam, isoxicam, tenoxicam, and sudoxicam; 2) the salicylates, such as aspirin, disalcid, benorylate, trilisate, safapryn, solprin, diflunisal, and fendosal; 3) the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac; 4) the fenamates, such as mefenamic, meclofenamic, flufenamic, niflumic, and tolfenamic acids; 5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and 6) the pyrazoles, such as phenylbutazone, oxyphenbutazone, feprazone, azapropazone, and trimethazone, mixtures of these non-steroidal anti-inflammatory agents may also be employed, as well as the pharmaceutically-acceptable salts and esters of these agents.

Anti-Bacterial Agents

In some embodiments, a contemplated formulation comprises medium chain fatty acids, or esters thereof; an omega 3 fatty acid or ester; at least one isoform of vitamin E; and an anti-bacterial agent. Suitable anti-antibacterial agents include sulfonamides, diaminopyrimidines, quinolones, beta-lactam antibiotics, cephalosporins, tetracyclines, notribenzene derivatives, aminoglycosides, macrolide antibiotics, polypeptide antibiotics, nitrofuran derivatives, nitroimidazoles, nicotinin acid derivatives, polyene antibiotics, imidazole derivatives or glycopeptide, cyclic lipopeptides, glycylcyclines and oxazolidinones. In further embodiments, these antibiotics include but are not limited to sulphadiazine, sulfones—[dapsone (DDS) and paraaminosalicyclic (PAS)], sulfanilamide, sulfamethizole, sulfamethoxazole, sulfapyridine, trimethoprim, pyrimethamine, nalidixic acids, norfloxacin, ciprofloxin, cinoxacin, enoxacin, gatifloxacin, gemifloxacin, grepafloxacin, levofloxacin, lomefloxacin, moxifloxacin, ofloxacin, pefloxacin, sparfloxacin, trovafloxacin, penicillins (amoxicillin, ampicillin, azlocillin, aarbenicillin, cloxacillin, dicloxacillin, flucloxacillin, hetacillin, oxacillin, mezlocillin, penicillin G, penicillin V, piperacillin), cephalosporins (cefacetrile, cefadroxil, cefalexin, cefaloglycin, cefalonium, cefaloridin, cefalotin, cefapirin, cefatrizine, cefazaflur, cefazedone, cefazolin, cefradine, cefroxadine, ceftezole, cefaclor, cefonicid, ceforanide, cefprozil, cefuroxime, cefuzonam, cefmetazole, cefoteta, cefoxitin, cefcapene, cefdaloxime, cefdinir, cefditoren, cefetamet, cefixime, cefmenoxime, cefodizime, cefoperazone, cefotaxime, cefotiam, cefpimizole, cefpiramide, cefpodoxime, cefteram, ceftibuten, ceftiofur, ceftiolen, ceftizoxime, ceftriaxone, cefoperazone, ceftazidime, cefepime), moxolactam, carbapenems (imipenem, ertapenem, meropenem) monobactams (aztreonam), oxytetracycline, chlortetracycline, clomocycline, demeclocycline, tetracycline, doxycycline, lymecycline, meclocycline, methacycline, minocycline, rolitetracycline, chloramphenicol, amikacin, gentamicin, framycetin, kanamycin, neomicin, neomycin, netilmicin, streptomycin, tobramycin, azithromycin, clarithromycin, dirithromycin, erythromycin, roxithromycin, telithromycin, colistin, bacitracin, tyrothricin, notrifurantoin, furazolidone, metronidazole, tinidazole, isoniazid, pyrazinamide, ethionamide, nystatin, amphotericin-B, hamycin, miconazole, clotrimazole, ketoconazole, fluconazole, rifampacin, lincomycin, clindamycin, spectinomycin, chloramphenicol, clindamycin, colistin, fosfomycin, loracarbef, metronidazole, nitrofurantoin, polymyxin B, polymyxin B sulfate, procain, ramoplanin, teicoplanin, and vancomycin, and combinations thereof.

Anti-Oxidants

In some embodiments, a contemplated formulation comprises medium chain fatty acids, or esters thereof; an omega 3 fatty acid or ester; at least one isoform of vitamin E; and an agent that reduces oxidative stress, e.g., an anti-oxidant. Suitable anti-oxidants include, but are not limited to, NXY-059 (Disufenton sodium); chain-breaking phenolic antioxidants (such as Vitamin E and butylated hydroxytoluene [BHT]); phenyl-substituted nitrones; azulenyl-substituted nitrones; alpha-phenyl-N-tert-butyl nitrone; stilbazulenyl nitrone (STAZN; Becker et al. (2002) J. Am. Chem. Soc. 124:4678); a spin-trap agent such as, e.g., N-t-butyl-a-phenylnitrone, 3,5-dibromo-4-nitrosobenzenesulfonic acid, 5,5-dimethyl-1-pyrroline N-oxide, 2-methyl-2-nitrosopropane, nitrosodisulfonic acid, a-(4-pyridyl-1-oxide)-N-t-butylnitrone, 3,3,5,5-tetramethylpyrroline N-oxide, 2,4,6-tri-t-butylnitrosobenzene, PTIYO (4-phenyl-2,2,5,5-tetramethyl imidazolin-1-yloxy-5-oxide), tempol (4-hydroxy 2,2,6,6-tetramethylpiperidine-1-oxyl); and the like. An anti-oxidant can be a nitrone anti-oxidant (e.g., STAZN), a polyphenol anti-oxidant, a flavonol anti-oxidant (e.g., baicalein), or a phenylpropanoid anti-oxidant (e.g., chlorogenic acid, fisetin, etc.). Also suitable is an anti-oxidant as described in U.S. Patent Publication No. 2007/0275932.

Saccharides or Polysaccharides

In certain embodiments, a contemplated formulation comprises medium chain fatty acids, or esters thereof; an omega 3 fatty acid or ester; at least one isoform of vitamin E; and a saccharide (e.g., glucose) or polysaccharide. Such additional components can include, e.g., lactose, glucose, sucrose, corn starch, potato starch, cellulose esters such as cellulose acetate, ethyl cellulose, and microcrystalline cellulose.

Examples of suitable monosaccharides include sorbitol, mannitol, erythrose, threose, ribose, arabinose, xylose, ribulose, glucose, galactose, mannose, fructose, and sorbose. Non-limiting examples of suitable disaccharides include sucrose, maltose, lactitol, maltitol, maltulose, and lactose.

Suitable carbohydrates include oligosaccharides, polysaccharides, and/or carbohydrate derivatives. As used herein, the term "oligosaccharide" refers to a digestible linear molecule having from 3 to 9 monosaccharide units, wherein the units are covalently connected via glycosidic bonds. As used herein, the term "polysaccharide" refers to a digestible (i.e., capable of metabolism by the human body) macromolecule having greater than 9 monosaccharide units, wherein the units are covalently connected via glycosidic bonds. The polysaccharides may be linear chains or branched. Carbohydrate derivatives, such as a polyhydric alcohol (e.g., glycerol), may also be utilized as a complex carbohydrate herein. As used herein, the term "digestible" in the context of carbohydrates refers to carbohydrates that are capable of metabolism by enzymes produced by the human body. Examples of non-digestible carbohydrates are resistant starches (e.g., raw corn starches) and retrograded amyloses (e.g., high amylose corn starches). Non-limiting examples of suitable carbohydrates include raffinoses, stachyoses, maltotrioses, maltotetraoses, glycogens, amyloses, amylopectins, polydextroses, and maltodextrins.

Suitable starches include natural starches, e.g., starches derived from a natural source, such as those obtained from various plant species. Examples of plant sources of starch include, but are not limited to, corn, waxy corn, wheat, rice, tapioca, potato, pea and other sources known in the art. Suitable starches include modified starches. Modified starches are known in the art and the term generally refers to starch that has been physically or chemically altered to improve its functional characteristics. Suitable modified starches include, but are not limited to, pre-gelatinized starches, low viscosity starches (such as dextrins, acid-modified starches, oxidized starches and enzyme modified starches), derivatized starches, stabilized starches (such as starch esters and starch ethers), cross-linked starches, starch sugars (such as glucose syrup, dextrose and isoglucose) and starches that have been submitted to a combination of treatments (such as cross-linking and gelatinization) and mixtures thereof.

Suitable modified cellulose gums include, for example, methylcellulose (MC), hydroxypropyl methylcellulose (HPMC), ethyl cellulose (EC), hydroxyethyl cellulose (HEC), hydroxypropylcellulose (HPC), hydroxypropyl methylcellulose acetate, hydroxyethyl methylcellulose, hydroxyethylcellulose acetate, hydroxyethyl ethylcellulose and combinations thereof.

Food-Grade Components and Pharmaceutically Acceptable Excipients

In certain embodiments, a contemplated formulation comprises medium chain fatty acids, or esters thereof an omega 3 fatty acid or ester; at least one isoform of vitamin E; food components and a pharmaceutically acceptable excipients. Components such as magnesium stearate, calcium silicate, precipitated silica, talc, fatty acids such as stearic acid, carnauba wax and the like are contemplated. Diluents and other additives such as one or more pharmaceutically acceptable binding agents, fillers, supports, thickening agents, taste-improving agents, coloring agents, preservatives, stabilizers, regulators, emulsifiers, flow agents, absorbents, and the like or mixtures thereof may be used depending on the form of the composition employed.

In some embodiments, a subject formulation further includes one or more food-grade components. Suitable components include, but are not limited to, proteins; amino acids; fatty acids; lipids; stabilizers; preservatives; flavoring agents; coloring agents; sweeteners; antioxidants, chelators, and carriers; texturants; pH adjusters; emulsifiers; stabilizers; soy and soy-based components; milk base solids; edible fibers; and the like. The food component can be isolated from a natural source, or can be synthesized. All components are food-grade components fit for human consumption.

In some embodiments, a contemplated formulation that comprises one or more food components is gluten free. In some embodiments, a contemplated formulation that comprises one or more food components is casein free. In some embodiments, a contemplated formulation that comprises one or more food components is gluten free and casein free. "Gluten free" means that a subject formulation contains substantially no gluten; or, if the formulation does contain gluten, the gluten is present in an amount that does not induce an adverse reaction in an individual who is gluten sensitive (e.g., allergic to gluten) or who is gluten intolerant. Similarly, "casein free" means that a contemplated formulation contains substantially no gluten; or, if the formulation does contain gluten, the gluten is present in an amount that does not induce an adverse reaction in an individual who is casein sensitive (e.g., allergic to casein) or who is casein intolerant.

Suitable texturants (also referred to as soluble fibers) include, but are not limited to, pectin (high ester, low ester); carrageenan; alginate (e.g., alginic acid, sodium alginate, potassium alginate, calcium alginate); guar gum; locust bean gum; *psyllium*; xanthan gum; gum arabic; fructo-oligosaccharides; inulin; agar; a modified cellulose gum; and functional blends of two or more of the foregoing.

Suitable emulsifiers include, but are not limited to, propylene glycol monostearate (PGMS), sodium stearoyl lactylate (SSL), calcium stearoyl lactylate (CSL), monoglycerides, diglycerides, monodiglycerides, polyglycerol esters, lactic acid esters, polysorbate, sucrose esters, diacetyl tartaric acid esters of mono-diglycerides (DATEM), citric acid esters of monoglycerides (CITREM) and combinations thereof. Additional suitable emulsifiers include DIMODAN, including DIMODAN™ B 727 and DIMODAN™ PV, GRINDSTED™ CITREM, GRINDSTED™ GA, GRINDSTED™ PS such as GRINDSTED™ PS 100, GRINDSTED™ PS 200, GRINDSTED™ PS 300, GRINDSTED™ PS 400; RYLO™ (manufactured and distributed by DANISCO CULTOR), including RYLO™ AC, RYLO™ CI, RYLO™ LA, RYLO™ MD, RYLO™ MG, RYLO™ PG, RYLO™ PR, RYLO™ SL, RYLO™ SO, RYLO™ TG; and combinations thereof.

Edible fibers include polysaccharides, oligosaccharides, lignin and associated plant substances. Suitable edible fibers include, but are not limited to, sugar beet fiber, apple fiber, pea fiber, wheat fiber, oat fiber, barley fiber, rye fiber, rice fiber, potato fiber, tomato fiber, other plant non-starch polysaccharide fiber, and combinations thereof.

Suitable flavoring agents include natural and synthetic flavors, "brown flavorings" (e.g., coffee, tea); dairy flavorings; fruit flavors; vanilla flavoring; essences; extracts; oleoresins; juice and drink concentrates; flavor building blocks (e.g., delta lactones, ketones); and the like; and combinations of such flavors. Examples of botanic flavors include, for example, tea (e.g., preferably black and green tea), aloe vera, guarana, *ginseng*, ginkgo, hawthorn, hibiscus, rose hips, chamomile, peppermint, fennel, ginger, licorice, lotus seed, schizandra, saw palmetto, sarsaparilla, safflower, St. John's Wort, *curcuma*, cardamom, nutmeg, *cassia* bark, buchu, cinnamon, jasmine, haw, *chrysanthemum*, water chestnut, sugar cane, lychee, bamboo shoots, vanilla, coffee, and the like.

Suitable sweeteners include, but are not limited to, alitame; dextrose; fructose; lactilol; polydextrose; xylitol; xylose; aspartame, saccharine, cyclamates, acesulfame K, L-aspartyl-L-phenylalanine lower alkyl ester sweeteners, L-aspartyl-D-alanine amides; L-aspartyl-D-serine amides; L-aspartyl-hydroxymethyl alkane amide sweeteners; L-aspartyl-1-hydroxyethylalkane amide sweeteners; and the like.

Suitable anti-oxidants include, but are not limited to, tocopherols (natural, synthetic); ascorbyl palmitate; gallates; butylated hydroxyanisole (BHA); butylated hydroxytoluene (BHT); tert-butyl hydroquinone (TBHQ); and the like.

Suitable coloring agents include, but are not limited to, FD&C dyes (e.g., yellow #5, blue #2, red #40), FD&C lakes; Riboflavin; beta-carotene; natural coloring agents, including, for example, fruit, vegetable, and/or plant extracts such as grape, black currant, *aronia*, carrot, beetroot, red cabbage, and hibiscus.

Exemplary Preservatives Include Sorbate, Benzoate, and Polyphosphate Preservatives.

Suitable emulsifiers include, but are not limited to, diglycerides; monoglycerides; acetic acid esters of mono- and diglycerides; diacetyl tartaric acid esters of mono- and diglycerides; citric acid esters of mono- and diglycerides; lactic acid esters of mono- and diglycerides; fatty acids; polyglycerol esters of fatty acids; propylene glycol esters of fatty acids; sorbitan monostearates; sorbitan tristearates; sodium stearoyl lactylates; calcium stearoyl lactylates; and the like.

Suitable agents for pH adjustment include organic as well as inorganic edible acids. The acids can be present in their undissociated form or, alternatively, as their respective salts, for example, potassium or sodium hydrogen phosphate, potassium or sodium dihydrogen phosphate salts. Exemplary acids are edible organic acids which include citric acid, malic acid, fumaric acid, adipic acid, phosphoric acid, gluconic acid, tartaric acid, ascorbic acid, acetic acid, phosphoric acid and mixtures thereof.

A contemplated formulation can be prepared in a variety of ways for consumption by an individual, and, as indicated above, can include one or more food components. Food formulations can be in a variety of forms, including powders; liquids; gels; and solid forms such as bars, tablets, capsules, candies, etc. Formulations of interest include foods for veterinary or human use, including food bars (e.g. cereal bars, breakfast bars, energy bars, nutritional bars); drinks; fortified drinks; carbonated beverages; drink supplements (e.g., powders to be added to a drink); powders to be mixed with food; tablets; lozenges; candy; candy-like formulations, e.g., chewable gel formulations, e.g., chewable gel candy in the shape of an animal; puddings; and the like. Suitable food formulations also include those described in U.S. Pat. No. 7,067,150.

A food product can have final moisture content between about 0% and about 100%, e.g., from about 0% to about 1%, from about 1% to about 5%, from about 5% to about 10%, from about 10% to about 30%, from about 30% to about 50%, from about 50% to about 80%, or from about 80% to about 100%.

Packages

The present disclosure further provides a package comprising a contemplated formulation. In some embodiments, a contemplated package comprises a single dosage form of a contemplated formulation. In other embodiments, a contemplated package comprises multiple (e.g., 2, 3, 4, 5, 6, 7, 8, 9, 10, or more) dosage forms.

As one non-limiting example, a subject food product can be packaged in such a way that multiple doses are contained in a single package, optionally where individual unit dosage forms are separated in individual compartments in a single package. The dosage forms can be in a variety of forms, e.g., tablets or lozenges that are palatable (e.g., flavored so as to be palatable, such as with fruit flavorings, sugars, and the like, as discussed above). Unit dosage forms include tablets, capsules, lozenges, candies, bars, a unit of powder (e.g., 1 tablespoon of a powder; a unit of a liquid, (e.g., a 1 tablespoon of a liquid), etc.

In some embodiments, a contemplated package will further include instructions for use, including e.g., dosage amounts and dosage frequencies. Instructions are in some embodiments printed directly on the package. In other embodiments, instructions are printed material provided as a package insert. Instructions can also be provided in other media, e.g., electronically in digital or analogue form, e.g., on an audio cassette, an audio tape, a compact disc, a digital versatile disk, and the like.

Exemplary Formulations

The following are exemplary formulations. As noted above, in addition to the components specifically listed below, a contemplated formulation can include one or more additional active and/or inactive components, food-grade components, etc. In the exemplary formulations below, amounts are given as per unit dose. In certain embodiments, the components of the formulations below (1-30) are in a softgel further comprising gelatin, purified water and, glycerine. The medium chain fatty acid glycol esters are from Douglas Lab (MCT) liquid approximately caprylic (C8) 70-60% and capric (C10) 40-30%, and less than 5% of other fatty acids.

Exemplary Formulation 1 Exemplary Formulation 2

| Component | Amount |
| --- | --- |
| MCT | 1000 mg |
| EPA | 700 mg |
| DHA | 250 mg |
| Alpha-tocopherol | 500 mg |
| Gamma-tocopherol | 200 mg |

| Component | Amount |
| --- | --- |
| MCT | 10 g |
| EPA | 700 mg |
| DHA | 250 mg |
| Alpha-tocopherol | 1500 mg |
| Gamma-tocopherol | 600 mg |

In some embodiments, the amount of MCT in Exemplary formulation 1 is increased from 1000 mg to 3000 mg.

Exemplary Formulation 3 Exemplary Formulation 4

| Component | Amount |
| --- | --- |
| MCT | 12 g |
| EPA | 700 mg |
| DHA | 250 mg |
| Alpha-tocopherol | 500 mg |
| Gamma-tocopherol | 200 mg |
| Alpha-lipoic acid | 100 mg |

| Component | Amount |
| --- | --- |
| MCT | 1000 mg |
| EPA | 700 mg |
| DHA | 250 mg |
| Alpha-tocopherol | 1500 mg |
| Gamma-tocopherol | 600 mg |
| Alpha-lipoic acid | 600 mg |

Exemplary Formulation 5 Exemplary Formulation 6

| Component | Amount |
| --- | --- |
| MCT | 12 g |
| EPA | 700 mg |
| DHA | 250 mg |
| Alpha-tocopherol | 1500 mg |
| Gamma-tocopherol | 600 mg |
| Carnitine | 3000 mg |

| Component | Amount |
| --- | --- |
| MCT | 1000 mg |
| EPA | 700 mg |
| DHA | 165 mg |
| Alpha-tocopherol | 500 mg |
| Gamma-tocopherol | 200 mg |
| Carnitine | 200 mg |

Exemplary Formulation 7 Exemplary Formulation 8

| Component | Amount |
| --- | --- |
| MCT | 1000 mg |
| EPA | 700 mg |
| DHA | 250 mg |
| GLA | 70 mg |
| Alpha-tocopherol | 1500 mg |
| Gamma-tocopherol | 600 mg |

| Component | Amount |
| --- | --- |
| MCT | 1000 mg |
| EPA | 700 mg |
| DHA | 250 mg |
| GLA | 70 mg |
| Alpha-tocopherol | 500 mg |
| Gamma-tocopherol | 200 mg |

Exemplary Formulation 9 Exemplary Formulation 10

| Component | Amount |
| --- | --- |
| MCT | 1000 mg |
| EPA | 700 mg |
| DHA | 250 mg |
| GLA | 70 mg |
| Oleic acid | 250 mg |
| Alpha-tocopherol | 1500 mg |

| Component | Amount |
|---|---|
| Gamma-tocopherol | 600 mg |

| Component | Amount |
|---|---|
| MCT | 1000 mg |
| EPA | 700 mg |
| DHA | 250 mg |
| GLA | 70 mg |
| Oleic acid | 250 mg |
| Alpha-tocopherol | 500 mg |
| Gamma-tocopherol | 200 mg |

Exemplary Formulation 11 Exemplary Formulation 12

| Component | Amount |
|---|---|
| MCT | 1000 mg |
| EPA | 700 mg |
| DHA | 250 mg |
| GLA | 70 mg |
| Oleic acid | 250 mg |
| Alpha-tocopherol | 500 mg |
| Gamma-tocopherol | 200 mg |
| Alpha-lipoic acid | 100 mg |

| Component | Amount |
|---|---|
| MCT | 1000 mg |
| EPA | 700 mg |
| DHA | 250 mg |
| GLA | 70 mg |
| Oleic acid | 250 mg |
| Alpha-tocopherol | 1500 mg |
| Gamma-tocopherol | 600 mg |
| Alpha-lipoic acid | 600 mg |

Exemplary Formulation 13 Exemplary Formulation 14

| Component | Amount |
|---|---|
| MCT | 1000 mg |
| EPA | 700 mg |
| DHA | 250 mg |
| GLA | 70 mg |
| Oleic acid | 250 mg |
| Alpha-tocopherol | 500 mg |
| Gamma-tocopherol | 200 mg |
| Alpha-lipoic acid | 100 mg |
| Carnitine | 200 mg |

| Component | Amount |
|---|---|
| MCT | 1000 mg |
| EPA | 700 mg |
| DHA | 250 mg |
| GLA | 70 mg |
| Oleic acid | 250 mg |
| Alpha-tocopherol | 1500 mg |
| Gamma-tocopherol | 600 mg |
| Alpha-lipoic acid | 600 mg |
| Carnitine | 3000 mg |

Exemplary Formulation 15 Exemplary Formulation 16

| Component | Amount |
|---|---|
| MCT | 1000 mg |
| EPA | 700 mg |
| DHA | 250 mg |
| GLA | 70 mg |
| Oleic acid | 200 mg |
| Alpha-tocopherol | 500 mg |
| Gamma-tocopherol | 200 mg |
| Alpha-lipoic acid | 100 mg |
| Carnitine | 1000 mg |

| Component | Amount |
|---|---|
| MCT | 1000 mg |
| EPA | 700 mg |
| DHA | 250 mg |
| GLA | 70 mg |
| Oleic acid | 250 mg |
| Alpha-tocopherol | 1500 mg |
| Gamma-tocopherol | 600 mg |
| Alpha-lipoic acid | 200 mg |
| Carnitine | 3000 mg |

Exemplary Formulation 17 Exemplary Formulation 18

| Component | Amount |
|---|---|
| MCT | 1000 mg |
| EPA | 700 mg |
| DHA | 250 mg |
| GLA | 70 mg |
| Oleic acid | 250 mg |
| Alpha-tocopherol | 500 mg |
| Gamma-tocopherol | 200 mg |
| Alpha-lipoic acid | 100 mg |
| Carnitine | 1000 mg |
| Vitamin C | 250 mg |

| Component | Amount |
|---|---|
| MCT | 1000 mg |
| EPA | 700 mg |
| DHA | 250 mg |
| GLA | 70 mg |
| Oleic acid | 250 mg |
| Alpha-tocopherol | 1500 mg |
| Gamma-tocopherol | 600 mg |
| Alpha-lipoic acid | 600 mg |
| Carnitine | 3000 mg |
| Vitamin C | 500 mg |

Exemplary Formulation 19 Exemplary Formulation 20

| Component | Amount |
|---|---|
| MCT | 1000 mg |
| EPA | 700 mg |
| DHA | 250 mg |
| GLA | 70 mg |
| Oleic acid | 250 mg |
| Alpha-tocopherol | 500 mg |
| Gamma-tocopherol | 200 mg |
| Alpha-lipoic acid | 100 mg |
| Carnitine | 200 mg |
| Vitamin C | 250 mg |
| Phosphocholine | 1 g |

| Component | Amount |
| --- | --- |
| MCT | 1000 mg |
| EPA | 700 mg |
| DHA | 250 mg |
| GLA | 70 mg |
| Oleic acid | 250 mg |
| Alpha-tocopherol | 1500 mg |
| Gamma-tocopherol | 600 mg |
| Alpha-lipoic acid | 600 mg |
| Carnitine | 3000 mg |
| Vitamin C | 500 mg |
| Phosphocholine | 3 g |

Exemplary Formulation 21 Exemplary Formulation 22

| Component | Amount |
| --- | --- |
| MCT | 1000 mg |
| EPA | 700 mg |
| DHA | 250 mg |
| GLA | 70 mg |
| Oleic acid | 250 mg |
| Alpha-tocopherol | 500 mg |
| Gamma-tocopherol | 200 mg |
| Alpha-lipoic acid | 100 mg |
| Carnitine | 200 mg |
| Vitamin C | 250 mg |
| Phosphocholine | 1 g |
| Zinc | 15 mg |

| Component | Amount |
| --- | --- |
| MCT | 1000 mg |
| EPA | 700 mg |
| DHA | 250 mg |
| GLA | 70 mg |
| Oleic acid | 250 mg |
| Alpha-tocopherol | 1500 mg |
| Gamma-tocopherol | 600 mg |
| Alpha-lipoic acid | 600 mg |
| Carnitine | 3000 mg |
| Vitamin C | 500 mg |
| Phosphocholine | 3 g |
| Zinc | 30 mg |

Exemplary Formulation 23 Exemplary Formulation 24

| Component | Amount |
| --- | --- |
| MCT | 1000 mg |
| EPA | 700 mg |
| DHA | 250 mg |
| GLA | 70 mg |
| Oleic acid | 250 mg |
| Alpha-tocopherol | 500 mg |
| Gamma-tocopherol | 200 mg |
| Alpha-lipoic acid | 100 mg |
| Carnitine | 200 mg |
| Vitamin C | 250 mg |
| Phosphocholine | 1 g |
| Zinc | 15 mg |
| Vitamin K | 5 μg |

| Component | Amount |
| --- | --- |
| MCT | 1000 mg |
| EPA | 700 mg |
| DHA | 250 mg |
| GLA | 70 mg |
| Oleic acid | 250 mg |
| Alpha-tocopherol | 1500 mg |
| Gamma-tocopherol | 600 mg |
| Alpha-lipoic acid | 600 mg |
| Carnitine | 3000 mg |
| Vitamin C | 500 mg |
| Phosphocholine | 3 g |
| Zinc | 30 mg |
| Vitamin K | 10 mg ($K_1 + K_2$) |

Exemplary Formulation 25 Exemplary Formulation 26

| Component | Amount |
| --- | --- |
| MCT | 1000 mg |
| EPA | 700 mg |
| DHA | 250 mg |
| GLA | 70 mg |
| Oleic acid | 200 mg |
| Alpha-tocopherol | 500 mg |
| Gamma-tocopherol | 200 mg |
| Alpha-lipoic acid | 100 mg |
| Carnitine | 500 mg |
| Vitamin C | 100 mg |
| Phosphocholine | 1 g |
| Zinc | 5 mg |
| Vitamin $K_1$ | 3 mg |
| Vitamin $K_2$ | 350 μg |

| Component | Amount |
| --- | --- |
| MCT | 1000 mg |
| EPA | 700 mg |
| DHA | 250 mg |
| GLA | 70 mg |
| Oleic acid | 200 mg |
| Alpha-tocopherol | 1500 mg |
| Gamma-tocopherol | 500 mg |
| Alpha-lipoic acid | 200 mg |
| Carnitine | 2000 mg |
| Vitamin C | 500 mg |
| Phosphocholine | 3 g |
| Zinc | 15 mg |
| Vitamin $K_1$ | 10 mg |
| Vitamin $K_2$ | 1 mg |

Exemplary Formulation 27 Exemplary Formulation 28

| Component | Amount |
| --- | --- |
| MCT | 24 g |
| EPA | 700 mg |
| DHA | 250 mg |
| GLA | 70 mg |
| Oleic acid | 200 mg |
| Alpha-tocopherol | 1500 mg |
| Gamma-tocopherol | 500 mg |
| Alpha-lipoic acid | 200 mg |
| Carnitine | 2000 mg |
| Vitamin C | 500 mg |
| Phosphocholine | 3 g |
| Zinc | 15 mg |
| Vitamin $K_1$ | 10 mg |
| Vitamin $K_2$ | 1 mg |
| Arginine | 3000 mg |
| Co-enzyme Q | 200 mg |
| Selenium | 50 μg |
| Vitamin A | 3000 IU |

| Component | Amount |
| --- | --- |
| MCT | 1000 mg |
| EPA | 700 mg |
| DHA | 250 mg |

| Component | Amount |
| --- | --- |
| Thiamin (B$_1$) | 7.5 mg |
| Riboflavin (B$_2$) | 7.5 mg |
| Vitamin B$_6$ | 200 mg |
| Vitamin B$_{12}$ | 1 mg |
| Vitamin D | 400 IU |
| Calcium | 100 mg |
| Elemental magnesium | 200 mg |
| Biotin (B$_7$) | 50 µg |
| Folic acid | 400 µg |
| Pantothenic acid | 10 mg |
| Tetrahydrobiopterin | 50 mg |
| Niacin | 15 mg |

| Component | Amount |
| --- | --- |
| MCT | 10 g |
| Icosapent ethyl (ethyl ester of eicosapentaenoic acid) | 1 g |
| Alpha-tocopherol | 1500 mg |
| Gamma-tocopherol | 500 mg |
| Berberine | 400 mg |
| Creon (porcine-derived lipases, proteases, and amylases) | 6,000 USP units of lipase 19,000 USP units of protease 30,000 USP units of amylase |
| Starch | 50 g |

Exemplary Formulation 29 Exemplary Formulation 30

| Component | Amount |
| --- | --- |
| MCT | 10 g |
| EPA | 700 mg |
| DHA | 250 mg |
| GLA | 70 mg |
| Oleic acid | 200 mg |
| Alpha-tocopherol | 1500 mg |
| Gamma-tocopherol | 500 mg |
| Alpha-lipoic acid | 200 mg |
| Carnitine | 2000 mg |
| Vitamin C | 500 mg |
| Phosphocholine | 3 g |
| Zinc | 15 mg |
| Vitamin K$_1$ | 10 mg |
| Vitamin K$_2$ | 1 mg |
| Arginine | 3000 mg |

| | |
| --- | --- |
| MCT | 2 g |
| alpha tocopheral | 500 IU |
| Gamma tocopheral | 200 mg |

| Component | Amount |
| --- | --- |
| Vitamin K (K1 and K2) | 2.3 mg |
| EPA | 725 mg |
| DHA | 275 mg |
| GLA | 60 mg |
| Co-enzyme Q | 200 mg |
| Selenium | 50 µg |
| Vitamin A | 3000 IU |
| Thiamin (B$_1$) | 7.5 mg |
| Riboflavin (B$_2$) | 7.5 mg |
| Vitamin B$_6$ | 200 mg |
| Vitamin B$_{12}$ | 1 mg |
| Vitamin D | 400 IU |
| Calcium | 100 mg |
| Magnesium citrate | 200 mg |
| Biotin (B$_7$) | 50 µg |
| Folic acid | 400 µg |
| Pantothenic acid | 10 mg |
| Tetrahydrobiopterin | 50 mg |
| Niacin | 15 mg |
| N-acetylcysteine | 200 mg |
| Acetylsalicylic acid | 100 mg |
| Methylcobalamin | 1 mg |
| Folinic acid | 800 µg |
| Berberine | 400 mg |
| Creon (porcine-derived lipases, proteases, and amylases) | 6,000 USP units of lipase 19,000 USP units of protease 30,000 USP units of amylase |

Exemplary Formulation 31

MCT (1000 mg); EPA (700 mg); DHA (250 mg); Alpha-tocopherol (50 mg); Gamma-tocopherol (20 mg); Sodium Citrate (100 mg); Potassium Bicarbonate (300 mg); glucose (35 g); L-amino acids of L-Glutamine, L-Lysine Acetate, L-Leucine, L-Arginine Acetate, L-Valine, L-Isoleucine, L-Aspartic Acid, L-Alanine, L-Phenylalanine, L-Serine, L-Proline, L-Threonine, L-Tyrosine, L-Glutamic Acid, L-Histidine Hydrochloride, L-Methionine, L-Cystine, and L-Tryptophan (mixture of 6 g); β-carotene (400 µg); L-ascorbic acid (25 mg); Calcium carbonate (500 mg); Iron (mg 10); Cholecalciferol (10 µg); Phylloquinone (15 µg); Thiamin (1 mg); Riboflavin (1 mg); Niacin (5 mg); Pyridoxine (1 mg); Folic Acid (50 µg); Cobalamin (1 µg); Biotin (30 µg); Pantothenic Acid (2 mg); Calcium phosphate (300 mg); Iodine (30 µg; Magnesium sulfate (100 mg); Zinc gluconate (5 mg); Selenium Ascorbate (µg 10); Cupric sulfate (1 mg) Manganese citrate (1 mg), Chromium Acetate (20 µg); Molybdenum Citrate (20 µg); L-Carnitine (6 mg); Taurine (20 mg); Choline (60 mg), and myo-inositol (20 mg).

A contemplated formulation can be prepared as a single dosage form, or divided into two or more dosage forms. A contemplated formulation can comprise one unit dose; two unit doses; three unit doses; or more than three unit doses. For example, any of exemplary formulations 1-31 can be divided into two or more capsules, two or more tablets, two or more bars, two or more units of a powder (e.g., two or more grams of a powder, two or more tablespoons of a powder, etc.), two or more units liquid (e.g., two or more 1-ml units of a liquid, two or more 5-mL units of a liquid, etc.), two or more chewable gel units, or two or more units of another dosage form. Alternatively, a contemplated formulation can be a liquid formulation, where it can be formulated in a single dose (e.g., 1-15 mL) or formulated such that it is administered in two or more doses, where each dose is 1-10 mL). For example, exemplary formulations 1-31 provide the unit doses of the various components, which can be administered to an individual in one, two, three, four, or more, doses, which doses can be in various dosage forms, e.g., tablets, capsules, liquids, powders, food products, etc.

Methods of Use

In certain embodiments, the disclosure relates to methods of treating or preventing apraxia and/or autism spectrum disorder, the method comprising orally administering to an individual in need thereof an effective amount of a dietary formula disclosed herein. In certain embodiments, the disclosure relates to methods the subject is diagnosed with intestinal lymphangiectasia.

In certain embodiments, the intestinal lymphangiectasia is not occurring in isolation but together with the symptoms of apraxia/dyspraxia/autism spectrum disorders—symptoms which dramatically improve with aggressive nutrition particularly with omega 3 and fat soluble vitamins and minerals (zinc/magnesium) and medium chain acids and esters disclosed herein.

In certain embodiments, the disclosure relates to methods the formulation is administered once, twice, or three times daily, wherein said administration is effective to increase the percentile score of at least one of oral movement score, simple phonemic/syllabic score, complex phonemic/syllabic score, and spontaneous length and complexity score, by at least about 10, 20 or 30 percentile points.

In certain embodiments, the disclosure relates to methods of treating or preventing small bowel inflammation and conditions lending to small bowel bacterial overgrowth that induce fat malabsorption, the method comprising orally administering to an individual in need thereof an effective amount of a dietary formula disclosed herein to a subject in need thereof.

In certain embodiments, the disclosure relates to methods of treating an allergic disorder, the method comprising orally administering to an individual in need thereof an effective amount of the formulation disclosed herein wherein the disorder is selected from celiac disease, sprue, gluten sensitivity, a malabsorption syndrome, asthma, food allergy, leaky gut syndrome, and/or eczema.

In certain embodiments, the disclosure relates to methods of treating an inflammatory condition, the method comprising orally administering to an individual in need thereof an effective amount of a dietary formula disclosed herein, wherein the inflammatory condition is small intestinal bacterial overgrowth, rheumatic arthritis, diabetes, or cardiovascular disease.

In certain embodiments, the disclosure relates to methods of treating or preventing malnutrition and verbal apraxia or dyspraxia by administering effective amounts of nutritional formulas disclosed herein to a subject in need thereof. In certain embodiments, the subject is diagnosed with an autism spectrum disorder and intestinal lymphangiectasia, e.g., by video capsule endoscopy.

The present disclosure provides methods of treating various disorders, involving administering to an individual in need thereof an effective amount of a contemplated formulation. In certain embodiments, the method is useful for treating various disorders, including, but not limited to, apraxia, dyspraxia, autism, autism spectrum disorder, attention deficit/hyperactivity disorder, dyslexia, depression, sensory integration dysfunction; immune system disorders such as celiac disease, sprue, gluten sensitivity, a malabsorption syndrome, asthma, food allergy, leaky gut syndrome, and eczema; cardiovascular disease; diabetes; and inflammatory conditions such as rheumatoid arthritis.

In some embodiments, the method comprises administering a formula disclosed herein to an individual with apraxia, to treat the apraxia. In these embodiments, an effective amount of a subject formulation is an amount that, when administered in one or more doses, is effective to provide for an improvement in one or more of an oral movement score, a simple phonemic/syllabic score, a complex phonemic/syllabic score, and a spontaneous length and complexity score, e.g., in the Kaufman Praxis Test. For example, an effective amount of a subject formulation is an amount that, when administered in one or more doses, is effective to provide for an increase in percentile score of from about 5 to about 10 percentile, from about 10 to about 20 percentile, from about 20 to about 40 percentile, from about 40 to about 60 percentile, from about 60 to about 70 percentile, or from about 70 to about 90 percentile, on one or more of an oral movement score, a simple phonemic/syllabic score, a complex phonemic/syllabic score, and a spontaneous length and complexity score, e.g., in the Kaufman Praxis Test. Whether a subject formulation is effective in treating a disorder such as apraxia can be determined using well-established tests, such as the Kaufman Praxis Test.

A contemplated formulation is in some embodiments administered to an individual with an immune system disorder, to treat the immune system disorder. In these embodiments, an effective amount of the formulation is an amount that, when administered in one or more doses, is effective to provide for a reduction in one or more symptoms of an immune system disorder. For example, where the immune system disorder is an allergic disorder, an effective amount of a formulation is an amount that, when administered in one or more doses, is effective to provide for a reduction in circulating factor that is an indicator of an allergic disorder of from about 10% to about 20%, from about 20% to about 25%, from about 25% to about 30%, from about 30% to about 40%, from about 40% to about 50%, from about 50% to about 60%, from about 60% to about 70%, or from about 70% to about 80%, or more, of the level of the circulating factor present following exposure to an allergy-stimulating allergen. Circulating factors that are indicators of an allergic disorder include, e.g., allergen-specific IgE; inflammatory biomarkers; C-reactive protein; cytokines that are indicative of a Th2 immune response; and the like. As another example, where the immune system disorder is an allergic disorder, an effective amount of a formulation is an amount that, when administered in one or more doses, is effective to provide for one or more of: i) clinical improvement in one or more of sneezing, wheezing, runny nose, and other symptoms of an allergic reaction; ii) decreased number of visits to a medical personnel for treatment for the allergic disorder; and iii) decreased use of medications used to treat the symptoms of an allergic disorder. Whether a subject formulation is effective in treating an immune system disorder such as an allergic disorder can be determined using any well-established test, e.g., immunoassays for measuring IgE levels (e.g., allergen-specific IgE levels), and the like.

A contemplated formulation is administered, e.g., orally, to an individual in need thereof in any frequency deemed appropriate to treat the condition or disorder. For example, a formulation can be administered three times daily, twice daily, once daily, every other day, three times per week, twice per week, once per week, or less often. In some embodiments, a formulation is administered daily. In other embodiments, a formulation is administered every other day. For example, a unit dose of a contemplated formulation can be administered once, twice, or three times daily.

A contemplated formulation can be administered at any frequency, as discussed above, over any period of time, as necessary to treat the condition or disorder. Thus, a formulation can be administered over a period of time, e.g., from about one week to about one month, from about one month to about three months, from about three months to about 6 months, from about 6 months to about one year, from about one year to about three years, from about three years to about six years, from about six years to about 10 years, or more than 10 years.

The dosages of medium chain fatty acids and esters (glycerol esters), omega 3 fatty acids or esters, and vitamin E, as well as the dosages of additional components such as carnitine and alpha-lipoic acid, can vary according to various factors, including, e.g., the age of the individual, the weight of the individual, the genetic makeup of the individual, and the severity of symptoms exhibited by the individual to whom a subject formulation is administered. The following are general guidelines.

Where a subject formulation includes medium chain fatty acids and esters (glycerol esters), the dosage may ranges from about 100 mg/day to about 5000 mg/day, e.g., from about 100 mg/day to about 200 mg/day, from about 200 mg/day to about 300 mg/day, from about 300 mg/day to about 400 mg/day, from about 400 mg/day to about 500 mg/day, from about 500 mg/day to about 600 mg/day, from about 600 mg/day to about 700 mg/day, from about 700 mg/day to about 800 mg/day, from about 800 mg/day to about 900 mg/day, from about 900 mg/day to about 1000 mg/day, from about 1000 mg/day to about 1100 mg/day, from about 1100 mg/day to about 1200 mg/day, from about 1200 mg/day to about 1300 mg/day, from about 1300 mg/day to about 1400 mg/day, from about 1400 mg/day to about 1500 mg/day, from about 1500 mg/day to about 2000 mg/day, from about 2000 mg/day to about 3000 mg/day, from about 3000 mg/day to about 4000 mg/day, from about 4000 mg/day to about 5000 mg/day, from about 5 g/day to about 10 mg/day, from about 5 g/day to about 10 mg/day, from about 10 g/day to about 20 mg/day, from about 20 g/day to about 50 mg/day where the dosages given are for individual medium chain fatty acids or esters thereof or for total medium chain fatty acids or esters thereof (e.g., where more than one medium chain fatty acid glycol ester is present).

Where a subject formulation includes omega-3 fatty acids, the dosage of the omega-3 fatty acids ranges from about 100 mg/day to about 5000 mg/day, e.g., from about 100 mg/day to about 200 mg/day, from about 200 mg/day to about 300 mg/day, from about 300 mg/day to about 400 mg/day, from about 400 mg/day to about 500 mg/day, from about 500 mg/day to about 600 mg/day, from about 600 mg/day to about 700 mg/day, from about 700 mg/day to about 800 mg/day, from about 800 mg/day to about 900 mg/day, from about 900 mg/day to about 1000 mg/day, from about 1000 mg/day to about 1100 mg/day, from about 1100 mg/day to about 1200 mg/day, from about 1200 mg/day to about 1300 mg/day, from about 1300 mg/day to about 1400 mg/day, from about 1400 mg/day to about 1500 mg/day, from about 1500 mg/day to about 2000 mg/day, from about 2000 mg/day to about 3000 mg/day, from about 3000 mg/day to about 4000 mg/day, or from about 4000 mg/day to about 5000 mg/day, where the dosages given are for individual omega-3 fatty acids or for total omega-3 fatty acids (e.g., where more than one omega-3 fatty acid is present).

For example, in some embodiments, a contemplated formulation comprises the medium chain triglycerides which are the glycol esters of caprylic acid and capric acid, omega-3 fatty acids EPA and DHA. In some embodiments, the glycol esters glycol esters of caprylic acid and capric acid will range from about 50 mg/day to about 40 g/day, e.g., from about 500 mg/day to about 30 g/day, from about 1000 mg/day to about 20 g/day, from about 1000 mg/day to about 10 g/day, from about 2000 mg/day to about 10 mg/day, or from about 1000 mg/day to about 5 g/day.

In some embodiments, the dosage for EPA will range from about 500 mg/day to about 3000 mg/day, e.g., from about 500 mg/day to about 600 mg/day, from about 600 mg/day to about 700 mg/day, from about 700 mg/day to about 800 mg/day, from about 800 mg/day to about 900 mg/day, or from about 900 mg/day to about 1000 mg/day; and the dosage of DHA will range from about 100 mg/day to about 1000 mg/day, e.g., from about 100 mg/day to about 150 mg/day, from about 150 mg/day to about 200 mg/day, from about 200 mg/day to about 250 mg/day, from about 250 mg/day to about 300 mg/day, from about 300 mg/day to about 350 mg/day, from about 350 mg/day to about 400 mg/day, from about 400 mg/day to about 500 mg/day, from about 500 mg/day to about 600 mg/day, from about 600 mg/day to about 700 mg/day, from about 700 mg/day to about 800 mg/day, from about 800 mg/day to about 900 mg/day, or from about 900 mg/day to about 1000 mg/day.

The dosage of alpha-tocopherol ranges from about 10 mg/kg/day to about 200 mg/kg/day, e.g., from about 10 mg/kg/day to about 25 mg/kg/day, from about 25 mg/kg/day to about 50 mg/kg/day, from about 50 mg/kg/day to about 75 mg/kg/day, from about 75 mg/kg/day to about 100 mg/kg/day, from about 100 mg/kg/day to about 125 mg/kg/day, from about 125 mg/kg/day to about 150 mg/kg/day, from about 150 mg/kg/day to about 175 mg/kg/day, or from about 175 mg/kg/day to about 200 mg/kg/day; and the dosage of gamma-tocopherol ranges from about 100 mg/day to about 1000 mg/day, e.g., from about 100 mg/day to about 200 mg/day, from about 200 mg/day to about 300 mg/day, from about 300 mg/day to about 400 mg/day, from about 400 mg/day to about 500 mg/day, from about 500 mg/day to about 600 mg/day, from about 600 mg/day to about 700 mg/day, from about 700 mg/day to about 800 mg/day, from about 800 mg/day to about 900 mg/day, or from about 900 mg/day to about 1000 mg/day.

The dosage of other forms of vitamin E (e.g., beta-tocopherol, delta-tocopherol, alpha-tocotrienol, beta-tocotrienol, delta-tocotrienol, and gamma-tocotrienol), if present in a subject formulation, can range from about 5 mg/day to about 1000 mg/day, e.g., from about 5 mg/day to about 10 mg/day, from about 10 mg/day to about 25 mg/day, from about 25 mg/day to about 50 mg/day, from about 50 mg/day to about 75 mg/day, from about 75 mg/day to about 100 mg/day, from about 100 mg/day to about 125 mg/day, from about 125 mg/day to about 150 mg/day, from about 150 mg/day to about 175 mg/day, from about 175 mg/day to about 200 mg/day, from about 200 mg/day to about 250 mg/day, from about 250 mg/day to about 500 mg/day, from about 500 mg/day to about 750 mg/day, or from about 750 mg/day to about 1000 mg/day, where the dosages given are for the individual isoforms of vitamin E.

Where a subject formulation comprises one or more omega-6 fatty acids, the dosage of omega-6 fatty acid can range from about 50 mg/day to about 1000 mg/day, e.g., from about 50 mg/day to about 75 mg/day, from about 75 mg/day to about 100 mg/day, from about 100 mg/day to about 150 mg/day, from about 150 mg/day to about 200 mg/day, from about 200 mg/day to about 250 mg/day, from about 250 mg/day to about 300 mg/day, from about 300 mg/day to about 350 mg/day, from about 350 mg/day to about 400 mg/day, from about 400 mg/day to about 450 mg/day, from about 450 mg/day to about 500 mg/day, from about 500 mg/day to about 600 mg/day, from about 600 mg/day to about 700 mg/day, from about 700 mg/day to about 800 mg/day, from about 800 mg/day to about 900 mg/day, or from about 900 mg/day to about 1000 mg/day.

Where a subject formulation comprises one or more omega-9 fatty acids, the dosage of omega-9 fatty acid can range from about 50 mg/day to about 500 mg/day, e.g., from about 50 mg/day to about 75 mg/day, from about 75 mg/day to about 100 mg/day, from about 100 mg/day to about 150 mg/day, from about 150 mg/day to about 200 mg/day, from about 200 mg/day to about 250 mg/day, from about 250 mg/day to about 300 mg/day, from about 300 mg/day to about 350 mg/day, from about 350 mg/day to about 400 mg/day, from about 400 mg/day to about 450 mg/day, or from about 450 mg/day to about 500 mg/day.

Where a subject formulation comprises alpha-lipoic acid, the dosage of alpha-lipoic acid can range from about 10 mg/kg/day to about 50 mg/kg/day, e.g., from about 10 mg/kg/day to about 20 mg/kg/day, from about 20 mg/kg/day to about 25 mg/kg/day, from about 25 mg/kg/day to about 30 mg/kg/day, from about 30 mg/kg/day to about 40 mg/kg/day, or from about 40 mg/kg/day to about 50 mg/kg/day; or can range from about 50 mg/day to about 1000 mg/day, e.g., from about 50 mg/day to about 75 mg/day, from about 75 mg/day to about 100 mg/day, from about 100 mg/day to about 150 mg/day, from about 150 mg/day to about 200 mg/day, from about 200 mg/day to about 250 mg/day, from about 250 mg/day to about 300 mg/day, from about 300 mg/day to about 350 mg/day, from about 350 mg/day to about 400 mg/day, from about 400 mg/day to about 450 mg/day, from about 450 mg/day to about 500 mg/day, from about 500 mg/day to about 600 mg/day, from about 600 mg/day to about 700 mg/day, from about 700 mg/day to about 800 mg/day, from about 800 mg/day to about 900 mg/day, or from about 900 mg/day to about 1000 mg/day.

Where a subject formulation comprises carnitine, the dosage of carnitine can range from about 20 mg/kg/day to about 75 mg/kg/day, e.g., from about 20 mg/kg/day to about 25 mg/kg/day, from about 25 mg/kg/day to about 30 mg/kg/day, from about 30 mg/kg/day to about 30 mg/kg/day, from about 40 mg/kg/day to about 50 mg/kg/day, from about 50 mg/kg/day to about 60 mg/kg/day, or from about 60 mg/kg/day to about 75 mg/kg/day; or can range from about 150 mg/day to about 3000 mg/day, e.g., from about 150 mg/day to about 200 mg/day, from about 200 mg/day to about 250 mg/day, from about 250 mg/day to about 300 mg/day, from about 300 mg/day to about 350 mg/day, from about 350 mg/day to about 400 mg/day, from about 400 mg/day to about 450 mg/day, from about 450 mg/day to about 500 mg/day, from about 500 mg/day to about 600 mg/day, from about 600 mg/day to about 700 mg/day, from about 700 mg/day to about 800 mg/day, from about 800 mg/day to about 900 mg/day, from about 900 mg/day to about 1000 mg/day, from about 1000 mg/day to about 1250 mg/day, from about 1250 mg/day to about 1500 mg/day, from about 1500 mg/day to about 1750 mg/day, from about 1750 mg/day to about 2000 mg/day, from about 2000 mg/day to about 2250 mg/day, from about 2250 mg/day to about 2500 mg/day, from about 2500 mg/day to about 2750 mg/day, or from about 2750 mg/day to about 3000 mg/day.

Subjects Suitable for Treatment

Subjects suitable for treatment with a subject method include individuals who have been diagnosed with a disorder such as apraxia, dyspraxia, autism spectrum disorder, intestinal lymphangiectasia, a gastrointestinal disorder, small intestinal bacterial overgrowth, attention deficit/hyperactivity disorder, dyslexia, or depression, sensory integration dysfunction; or an immune system disorder such as celiac disease, sprue, gluten sensitivity, a malabsorption syndrome, asthma, food allergy, leaky gut syndrome, or eczema; a cardiovascular disease; diabetes; or an inflammatory condition such as rheumatoid arthritis. Subjects suitable for treatment with a subject method also include individuals who have been previously treated (with a treatment method other than a subject method) for a disorder such as those listed above, but who have failed treatment (e.g., failed to respond to the treatment), who have relapsed, or in whom the previous treatment method was contraindicated (e.g., due to adverse reaction, etc.).

In some embodiments, the individual is a sub-adult human, e.g., an infant (e.g., from about 1 month of age to about 12 months of age); a toddler (e.g., from about 12 months of age to about 3 years of age); a pre-school age child (e.g., from about 3 years of age to about 5 years of age); a child from about 5 years of age to about 9 years of age; a pre-teen from about 9 years of age to about 12 years of age; or a teenager (e.g., from about 13 years of age to about 19 years of age). In other embodiments, the individual is an adult human, e.g., a human at least 18-20 years old.

In some embodiments, the individual is a sub-adult human who has been diagnosed with apraxia. In some embodiments, the individual is a sub-adult human who has been diagnosed with autism spectrum disorder. In certain embodiments, the subject has attention deficit hyperactivity disorder or any type of inflammatory bowel disease (IBD) such as Crohn's disease and ulcerative colitis.

In some embodiments, the individual exhibits gluten sensitivity. In some embodiments, the individual has a human leukocyte antigen (HLA) allele that is associated with gluten sensitivity. For example, in some embodiments, the individual has an HLA DQ1 allele. In some embodiments, the individual has elevated levels of anti-gliadin antibodies.

EXAMPLES

Child with ADS Diagnosed with Intestinal Lymphangiectasia

A child diagnosed with an apraxia syndrome responded to omega 3 fatty-acid and vitamin E supplementation. Small intestinal lymphangiectasia was recently discovered on video-capsule endoscopy as part of the continuing work-up for malabsorption. Intestinal lymphangiectasia is characterized by obstruction of lymph drainage from the small intestine and lacteal dilation that distorts the villus architecture (See FIG. 1). Lymphatic vessel obstruction and elevated intestinal lymphatic pressure in turn cause lymphatic leakage into the intestinal lumen, thus resulting in malabsorption and protein-losing enteropathy. Intestinal lymphangiectasia is believed to be a "rare" condition. It is believed that, intestinal lymphangiectasia has not been reported in children with autism and/or apraxia. The pathology in the small intestine would commonly be missed by conventional endoscopy.

The immune dysfunction caused by intestinal lymphangiectasia could lead to increased risk of opportunistic infections, explaining chronic thrush beyond infancy, disseminated molluscum infection, recurrent skin infections, and difficult to treat recurrent small bowel bacterial overgrowth an additional condition that will contribute to malabsorption and malnutrition. It would also explain remarkable anecdotal reports of dramatic improvements in speech, neurocognitive abilities and motor coordination with nutritional interventions.

The white villi and/or spots (dilated lacteals), white nodules in the jejunum are observed on video capsule endoscopy are consistent with the diagnosis of intestinal lymphangiectasia. This taken together with a long-standing history of fat malabsorption, neurological symptoms of vitamin E deficiency, a protein-losing enteropathy with previously unexplained hypoalbuminemia, multiple micronutrient and vitamin deficiencies (zinc, iron, vit D, B12 etc), short stature, edema of the ankles and hands, hypocholesterolemia (cholesterol<100), and vulnerability to infections suggesting immune dysregulation (chronic thrush, disseminated molluscum contagiosum, recurrent skin, ear and sinus infections) explains the dramatic response to nutritional interventions in this child.

Speech, coordination, hypotonia and pain sensation improved dramatically with omega 3, medium chain triglycerides, and vitamine E supplementation. Further benefits were realized with a comprehensive nutritional approach which included supplementation for vitamins and minerals found to be deficient, treatments aimed at small intestine bacterial overgrowth, antifungals for thrush, amino acid supplements, creatine (patient had h/o low creatine), carnitine/mitochondrial cocktail (alpha lipoic acid, Co-Q10, B-vitamins, vitamin C), pancreatic enzymes and anti-inflammatory therapies that target inflammatory bowel disease. Since the protein malnutrition and nutritional deficiencies were numerous, due to the small bowel disease, a comprehensive nutritional approach led to significant recovery of growth and weight gain and improved neurobehavioral issues typical of apraxia as well as improved nutritional status.

An adequate gastrointestinal work-up is rarely done in children with autism and/or apraxia despite symptoms of pain, diarrhea/constipation, fat malabsorption and immune issues (frequent infections). Conventional endoscopy would miss it in the distal small intestine (jejunum or ileum). However intestinal lymphangiectasia would explain GI symptoms, fat malabsorption, vitamin and mineral deficiencies and frequent infections that many of these children are afflicted by. It also provides a plausible explanation for clinical improvements with aggressive nutrition.

This disclosure contemplates an improved nutritional supplement formulated to treat or prevent intestinal lymphangiectasia, and in certain instances children diagnosed with autism and a speech impediment. Given that intestinal lymphangiectasia is worsened by ingestion of fat that dilate the lacteals, a high quality protein, low fat diet is typically recommended. However low-fat diets for children can contribute to essential fatty acid deficiencies that can lead to adverse neuro-cognitive and behavior complications.

In certain embodiments, this disclosure relates to a nutritional formula comprising long-chain polyunsaturated fatty acids, medium chain triglycerides, and fat soluble vitamins (fat-soluble vitamins A, D, E and K) to overcome the fat malabsorption syndrome. Optionally ingredients include carnitine, alpha lipoic acid, co-Q10, B-vitamins and minerals such as zinc, magnesium, calcium. In certain embodiments, the nutritional formula further comprises a saccharide or polysaccharide, such as purified glucose. In certain embodiments, the nutritional formula further comprises amino acids including glutamine and all or any essential/non-essential amino acids, taurine, probiotics, creatine, SAMe (S-adenosylmethionine), berberine, n-acetylcysteine, and trimethylglycine.

Elemental Amino Acid Formula

One uses formulations with MCT, omega-3s, and vitamin E in combination with a nutritionally complete hypoallergenic, amino acid-based infant & pediatric formula (non-peptide/protein) that includes essential nutrients. This can be used as a supplement for the dietary management of protein maldigestion, malabsorption, intestinal lymphangiectasia, GI-tract impairment, small bowel bacterial overgrowth etc. or other conditions in which an amino acid-based diet is required—that has additional ingredients beyond the essential amino acids, that include poly unsaturated fatty acids (DHA/EPA etc), higher dose of vitamine E to maximize neurological development & function that is compromised in conditions of malabsorption/SIBO, and additional ingredients to aid digestion (pancreatic enzymes), address an abnormal gut microbiome (probiotics, berberine), and address inflammation and/or oxidative stress (curcumin, Sulforaphane, etc). There is an unmet need for these patients.

This formulation typically contains essential vitamins, micronutrients, amino acids and fats such as monosaccharides (glucose), Medium Chain Triglycerides (from Coconut and/or Palm Kernel Oil), Soybean Oil, Calcium Glycerophosphate, Magnesium Gluconate and less than 2% of L-Glutamine, L-Lysine Acetate, L-Leucine, L-Arginine Acetate, Potassium Chloride, L-Valine, Citric Acid, L-Isoleucine, L-Aspartic Acid, L-Alanine, L-Phenylalanine, L-Serine, L-Proline, L-Threonine, Sodium Citrate, L-Tyrosine, L-Glutamic Acid, Potassium Citrate, Glycine, L-Histidine Hydrochloride, L-Methionine, Choline Bitatrate, L-Cystine, Polyglycerol Esters of Fatty Acids, L-Tryptophan, Sodium Phosphate, Ascorbic Acid, Potassium Sorbate and BHA/BHT (to Maintain Freshness), M-Inositol, Taurine, Alpha-Tocopheryl Acetate, Ferrous Sulfate, L-Carnitine, Zinc Sulfate, Niacinamide, Calcium Pantothenate, Vitamin D3, Copper Gluconate, Vitamin A Palmitate, Manganese Sulfate, Pyridoxine Hydrochloride, Thiamine Hydrochloride, Riboflavin, Beta Carotene, Chromium Chloride, Sodium Molybdate, Folic Acid, Potassium Iodide, Biotin, Sodium Selenite, Phytonadione, Vitamin B12.

For example one can add to commercially available formulas of Vivonex and EleCare poly unsaturated fatty acids (DHA/EPA etc), higher dose of vitamin E to maximize neurological development & function that is compromised in conditions of malabsorption/SIBO, and additional ingredients to aid digestion (pancreatic enzymes), address an abnormal gut microbiome (probiotics, berberine), and address inflammation/oxidative stress (curcumin, Sulforaphane, etc) optionally with higher vitamin/mineral doses and optionally additional ingredients that support mitochondrial function (co-Q10/Lipoic Acid/Carnitine/high dose vit E/B complex), or ingredients that address inflammation/oxidative stress (sulforaphane, e.g., derived from broccoli sprouts), curcumin, or the abnormal gut microbiome (berberine).

The invention claimed is:

1. A method of treating autism spectrum disorder comprising orally administering daily to a subject diagnosed with an autism spectrum disorder, apraxia, and a gastrointestinal tract impairment, an effective amount of a dietary formulation comprising:
  a) a medium chain fatty acid, glycerol ester, or alkyl ester thereof,
  b) an omega-3 fatty acid, glycerol ester, or alkyl ester thereof,
  c) an omega-6 fatty acid, glycerol ester, or alkyl ester thereof, and
  d) a vitamin E isomer from 100 mg to 10,000 mg,
  e) 5-hydroxytryptophan, from 10 mg to 100 mg, f) sulforaphane from 500 micrograms to 5000 micrograms, and g) curcumin from 50 mg to 2500 mg; and wherein the dietary formulation comprises less than 2% long chain saturated fatty acids by weight of the total weight of fatty acids.

2. The method of claim 1, wherein the gastrointestinal tract impairment is intestinal lymphangiectasia.

3. The method of claim 1, wherein the gastrointestinal tract impairment is maldigestion.

4. The method of claim 1, wherein the gastrointestinal tract impairment is malabsorption.

5. The method of claim 1, wherein the gastrointestinal tract impairment is small intestinal bacterial overgrowth.

6. The method of claim 1, wherein the subject is a sub-adult from 12 months to 19 years of age.

7. The method of claim 6, wherein the sub-adult is from about 12 months of age to about 3 years of age.

8. The method of claim 6, wherein the sub-adult is from 3 years of age to 5 years of age.

9. The method of claim 6, wherein the sub-adult is 5 years of age to 9 years of age.

10. The method of claim 6, wherein the sub-adult is 9 years of age to 12 years of age.

11. The method of claim 6, wherein the sub-adult is 13 years of age to 19 years of age.

12. The method of claim 1, wherein the medium chain fatty acid or alkyl ester thereof is capric acid, ethyl caprate, caprylic acid, ethyl caprylate, hexanoic acid, ethyl hexanoate, or combinations thereof.

13. The method of claim 1, wherein the dietary formulation further comprises a vitamin K.

14. The method of claim 1, wherein the omega-3 fatty acid or alkyl ester thereof is alpha-linolenic acid, eicosapentaenoic acid, docosahexaenoic acid, ethyl linolenate, ethyl eicosapentaenoate, ethyl docosahexaenoate, or combinations thereof.

15. The method of claim 1, wherein the omega-3 fatty acid contains eicosapentaenoic acid and docosahexaenoic acid.

16. The method of claim 15, wherein a ratio of eicosapentaenoic acid and docosahexaenoic acid is in a range of from about 1.5:1 to about 5:1.

17. The method of claim 1, wherein the vitamin E isomer is alpha-tocopherol, gamma-tocopherol, or a combination thereof.

18. The method of claim 1, wherein the omega-6 fatty acid is gamma-linolenic acid.

19. The method of claim 1, wherein the dietary formulation comprises less than 1% long chain saturated fatty acids by weight of the total weight of fatty acids.

* * * * *